(12) United States Patent
Pandev et al.

(10) Patent No.: US 10,210,606 B2
(45) Date of Patent: Feb. 19, 2019

(54) SIGNAL RESPONSE METROLOGY FOR IMAGE BASED AND SCATTEROMETRY OVERLAY MEASUREMENTS

(71) Applicant: KLA-Tencor Corporation, Milpitas, CA (US)

(72) Inventors: Stilian Ivanov Pandev, Santa Clara, CA (US); Dzmitry Sanko, Vallejo, CA (US); Wei Lu, San Jose, CA (US); Siddharth Srivastava, Hayward, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 111 days.

(21) Appl. No.: 14/880,077

(22) Filed: Oct. 9, 2015

(65) Prior Publication Data

US 2016/0117847 A1 Apr. 28, 2016

Related U.S. Application Data

(60) Provisional application No. 62/063,932, filed on Oct. 14, 2014, provisional application No. 62/069,741, filed on Oct. 28, 2014.

(51) Int. Cl.
*G06T 7/00* (2017.01)
*G01N 21/956* (2006.01)
(Continued)

(52) U.S. Cl.
CPC ........... *G06T 7/001* (2013.01); *G01N 21/956* (2013.01); *G03F 7/70633* (2013.01); *G06T 7/33* (2017.01);
(Continued)

(58) Field of Classification Search
CPC ...................................................... G06T 7/001
See application file for complete search history.

(56) References Cited

U.S. PATENT DOCUMENTS

| 5,608,526 A | 3/1997 | Piwonka-Corle et al. |
| 5,859,424 A | 1/1999 | Norton et al. |

(Continued)

OTHER PUBLICATIONS

Yoann Blancquaert, et al., "Performance of ASML YieldStar mDBO overlay targets for advanced lithography nodes C028 and C014 overlay process control," Proc. SPIE 8681, Metrology, Inspection , and Process Control for Microlithography XXVII, 86811F (Apr. 18, 2013).

(Continued)

*Primary Examiner* — James M Pontius
(74) *Attorney, Agent, or Firm* — Spano Law Group; Joseph S. Spano

(57) ABSTRACT

Methods and systems for measuring overlay error between structures formed on a substrate by successive lithographic processes are presented herein. Two overlay targets, each having programmed offsets in opposite directions are employed to perform an overlay measurement. Overlay error is measured based on zero order scatterometry signals and scatterometry data is collected from each target at two different azimuth angles. In addition, methods and systems for creating an image-based measurement model based on measured, image-based training data are presented. The trained, image-based measurement model is then used to calculate values of one or more parameters of interest directly from measured image data collected from other wafers. The methods and systems for image based measurement described herein are applicable to both metrology and inspection applications.

18 Claims, 23 Drawing Sheets

(51) Int. Cl.
  *G03F 7/20* (2006.01)
  *G06T 7/33* (2017.01)
  *H04N 5/225* (2006.01)
(52) U.S. Cl.
  CPC .............. *G06T 2207/10056* (2013.01); *G06T 2207/20081* (2013.01); *G06T 2207/30148* (2013.01); *H04N 5/2256* (2013.01)

(56) References Cited

U.S. PATENT DOCUMENTS

| | | |
|---|---|---|
| 6,429,943 B1 | 8/2002 | Opsal et al. |
| 6,633,831 B2 | 10/2003 | Nikoonahad et al. |
| 6,734,967 B1 | 5/2004 | Piwonka-Corle et al. |
| 6,816,570 B2 | 10/2004 | Janik et al. |
| 6,895,075 B2 | 5/2005 | Yokhin et al. |
| 6,972,852 B2 | 12/2005 | Opsal et al. |
| 6,982,793 B1 | 1/2006 | Yang et al. |
| 7,277,172 B2 | 10/2007 | Kandel et al. |
| 7,317,531 B2 | 1/2008 | Mieher et al. |
| 7,385,699 B2 | 6/2008 | Mieher et al. |
| 7,478,019 B2 | 1/2009 | Zangooie et al. |
| 7,826,071 B2 | 11/2010 | Shchegrov et al. |
| 7,929,667 B1 | 4/2011 | Zhuang et al. |
| 7,933,026 B2 | 4/2011 | Opsal et al. |
| 8,525,993 B2 | 9/2013 | Rabello et al. |
| 9,710,728 B2* | 7/2017 | Pandev ................. G06K 9/4604 |
| 9,739,702 B2 | 8/2017 | Bringholtz et al. |
| 2004/0233440 A1* | 11/2004 | Mieher ................. G01N 21/956 356/401 |
| 2005/0195398 A1* | 9/2005 | Adel ..................... B82Y 10/00 356/401 |
| 2006/0065625 A1* | 3/2006 | Abdulhalim ........ G03F 7/70633 216/59 |
| 2006/0146347 A1* | 7/2006 | Smith .................... G01B 11/24 356/625 |
| 2009/0116035 A1* | 5/2009 | Shyu ................... G03F 7/70633 356/508 |
| 2009/0296075 A1 | 12/2009 | Hu et al. |
| 2009/0313589 A1* | 12/2009 | Hsu ..................... G03F 7/70633 716/136 |
| 2011/0001978 A1* | 1/2011 | Smilde .................... G03F 7/705 356/446 |
| 2011/0154272 A1 | 6/2011 | Hsu et al. |
| 2012/0120396 A1 | 5/2012 | Kandel et al. |
| 2013/0114085 A1 | 5/2013 | Wang et al. |
| 2014/0111791 A1 | 4/2014 | Manassen et al. |
| 2014/0172394 A1 | 6/2014 | Kuznetsov et al. |
| 2014/0222380 A1 | 8/2014 | Kuznetsov et al. |
| 2014/0233031 A1 | 8/2014 | Schaar et al. |
| 2014/0270469 A1 | 9/2014 | Rotem |
| 2014/0297211 A1 | 10/2014 | Pandev et al. |
| 2014/0316730 A1 | 10/2014 | Shchegrov et al. |
| 2015/0042984 A1 | 2/2015 | Pandev et al. |
| 2015/0046118 A1 | 2/2015 | Pandev et al. |
| 2016/0117812 A1* | 4/2016 | Pandev ................. G06T 7/0004 382/149 |
| 2016/0216197 A1 | 7/2016 | Bringoltz et al. |
| 2016/0327871 A1* | 11/2016 | Nooitgedagt ....... G03F 7/70466 |
| 2017/0277046 A1* | 9/2017 | Leung ................... G03F 9/7065 |

OTHER PUBLICATIONS

Henk-Jan H. Smilde, et al., "Optical Scatterometry for In-Die Sub-Nanometer Overlay Metrology," 2013 International Conference on Frontiers of Characterization and Metrology for Nanoelectronics (FCMN2013), Mar. 25-28, 2013, NIST, Gaithersburg, Maryland, USA.

Berta Dinu, et al., "Overlay control using scatterometry based metrology (SCOM) in production environment," Metrology, Inspection, and Process Control for Microlithography XXII, Proc. SPIE 6922, 69222S (Apr. 16, 2008).

International Search Report dated Jan. 27, 2016, for PCT Application No. PCT/US2015/055373 filed on Oct. 13, 2015 by KLA-Tencor Corporation, 3 pages.

* cited by examiner

SIGNAL RESPONSE METROLOGY FOR IMAGE BASED AND SCATTEROMETRY OVERLAY MEASUREMENTS

CROSS REFERENCE TO RELATED APPLICATIONS

The present application for patent claims priority under 35 U.S.C. § 119 from U.S. provisional patent application Ser. No. 62/063,932, entitled "Method and Apparatus of Measuring Overlay," filed Oct. 14, 2014, and from U.S. provisional patent application Ser. No. 62/069,741, entitled "On Device Signal Response Metrology Using Image Information," filed Oct. 28, 2014, the subject matter of each is incorporated herein by reference in its entirety.

TECHNICAL FIELD

The described embodiments relate to metrology systems and methods, and more particularly to methods and systems for improved scatterometry based overlay measurements and image based measurements.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition, overlay and other parameters of nanoscale structures.

Semiconductor devices are often fabricated by depositing a series of layers on a substrate. Some or all of the layers include various patterned structures. The relative position of structures both within particular layers and between layers is critical to the performance of completed electronic devices. Overlay refers to the relative position of overlying or interlaced structures on the same or different layers of a wafer. Overlay error refers to deviations from the nominal (i.e., desired) relative position of overlying or interlaced structures. The greater the overlay error, the more the structures are misaligned. If the overlay error is too great, the performance of the manufactured electronic device may be compromised.

Scatterometry overlay (SCOL) metrology techniques have been applied to the characterization of overlay errors. These methods are based primarily on differential measurements of optical signals corresponding to diffraction from pairs of targets each with programmed overlay offsets. The unknown overlay error is extracted based on these differential measurements.

In most existing methods, overlay error is characterized based on a metric sensitive to asymmetry of the structure. In one example, existing angle-resolved scatterometry overlay (SCOL) involves a characterization of the asymmetry between the +1 and −1 diffracted orders that is indicative of overlay error. However, relying on asymmetry as the indicator of overlay error is problematic because other asymmetries such as line profile asymmetry or beam illumination asymmetry couple into the overlay-generated asymmetry in the measurement signal. This results in an inaccurate measurement of overlay error.

In existing methods, overlay error is typically evaluated based on measurements of specialized target structures formed at various locations on the wafer by a lithography tool. The target structures may take many forms, such as a box in box structure. In this form, a box is created on one layer of the wafer and a second, smaller box is created on another layer. The localized overlay error is measured by comparing the alignment between the centers of the two boxes. Such measurements are taken at locations on the wafer where target structures are available.

Unfortunately, these specialized target structures often do not conform to the design rules of the particular semiconductor manufacturing process being employed to generate the electronic device. This leads to errors in estimation of overlay errors associated with actual device structures that are manufactured in accordance with the applicable design rules. For example, image-based overlay metrology often requires the pattern to be resolved with an optical microscope that requires thick lines with critical dimensions far exceeding design rule critical dimensions. In another example, angle-resolved SCOL often requires large pitch targets to generate sufficient signal at the +1 and −1 propagating diffraction orders from the overlay targets. In some examples, pitch values in the range 500-800 nm may be used. Meanwhile, actual device pitches for logic or memory applications (design rule dimensions) may be much smaller, e.g., in the range 100-400 nm, or even below 100 nm.

In one existing method, two double grating targets with programmed overlay shift of +d and −d are used to measure +1 and −1 diffraction order intensity of both targets. Asymmetry in the +1 and −1 diffraction order signals is a measure of overlay shift between layers in the stack. Measured asymmetry is linearly proportional to overlay error and the pair of targets is used to calculate the proportion. Further details are described in "Performance of ASML YieldStar µDBO overlay targets for advanced lithography nodes C028 and C014 overlay process control," Proc. SPIE 8681, Metrology, Inspection, and Process Control for Microlithography XXVII, 86811F (Apr. 18, 2013) and "Optical Scatterometry For In-Die Sub-Nanometer Overlay Metrology," 2013 International Conference on Frontiers of Characterization and Metrology for Nanoelectronics (FCMN2013), Mar. 25-28, 2013, NIST, Gaithersburg, Md., USA.

A disadvantage of this approach is that measurements of +1 and −1 diffraction order signals require large pitch, non-design rule targets. Another disadvantage is that the measurement sensitivity depends on properly matching the illumination wavelength to the grating pitch of the metrology targets. Since the available illumination wavelengths are typically limited, this limits overlay sensitivity especially when the layers between the gratings are opaque for the available wavelengths.

In another existing method, at least three double grating targets each with different, programmed overlay shifts are illuminated and zero order diffraction light is collected over a large band of incidence space. Signal differences between every pair of targets are calculated. The resulting combination of differential signals is proportional to overlay. Measured overlay and the known, programmed overlay of the targets are used to calculate overlay error. Further details are described in "Overlay control using scatterometry based metrology (SCOL™) in production environment," Metrology, Inspection, and Process Control for Microlithography XXII, Proc. of SPIE Vol. 6922, 69222S, (2008). A disadvantage of this approach is that six or eight cell targets are typically required to measure both X and Y overlay.

In some other examples, a model based approach to overlay measurement is employed. In one example, a model of a double-grating target is parameterized including an overlay parameter. Electromagnetic modeling of light scattering is used to simulate signals collected from the double-grating target. Nonlinear regression of the simulated signals is performed against measured signals to estimate overlay error. This approach requires accurate modeling of the structure and the material properties. The modeling effort is complex and time consuming, and the resulting regression routines require a large amount of computing effort and time to reach a result.

Future overlay metrology applications present challenges for metrology due to increasingly small resolution requirements and the increasingly high value of wafer area. Thus, methods and systems for improved overlay measurements are desired.

Image based measurements typically involve the recognition of specific target features (e.g., line segments, boxes, etc.) in an image and parameters of interest are calculated based on these features. Typically, the specialized target structures are specific to the image processing algorithm. For example, the line segments associated with an overlay target (e.g., box-in-box target, frame-in-frame target, advanced imaging metrology (AIM) target) are specifically designed to comply with the specifics of the algorithm. For this reason, traditional image based metrology algorithms cannot perform reliably with arbitrary targets or device structures.

In addition, information is lost because the algorithms are applied to limited areas of the image. By selecting particular line edges, etc. as the focal point for analysis, contributions that might be made by other pixels in the image are ignored.

Moreover, traditional image based algorithms are sensitive to process variations, asymmetry, and optical system errors as these algorithms lack a systematic way to capture the impact of these error sources on the captured images.

In semiconductor manufacture, and patterning processes in particular, process control is enabled by performing metrology on specific dedicated structures. These dedicated structures may be located in the scribe lines between dies, or within the die itself. The use of dedicated metrology structures may introduce significant measurement errors. Discrepancies between actual device structures and dedicated metrology targets limit the ability of metrology data to accurately reflect the status of the actual device features in the die. In one example, discrepancies arise due to location dependent differences in process loading, pattern density, or aberration fields because the dedicated metrology targets and actual device structures are not collocated. In another example, the characteristic feature sizes of the dedicated metrology structures and the actual device structure are often quite different. Hence, even if the dedicated metrology target and the actual device structure are in close proximity, discrepancies result from differences in size. Furthermore, dedicated metrology structures require space in the device layout. When sampling density requirements are high, dedicated metrology structures crowd out actual device structures.

Future metrology applications present challenges for image based metrology due to increasingly small resolution requirements and the increasingly high value of wafer area. Thus, methods and systems for improved image based measurements are desired.

SUMMARY

Methods and systems for measuring overlay error between structures formed on a substrate by successive lithographic processes are presented herein. Overlay error is measured based on 0th order scatterometry signals. In one aspect, only two overlay targets are employed to perform an overlay measurement. Each of the two overlay targets each include a programmed overlay offset in a direction opposite one another. Scatterometry data is collected from each target at two different azimuth angles to produce symmetric signals. The symmetric signals are used to determine overlay error.

In a further aspect, the overlay measurement techniques described herein are applied to scatterometry signals including multiple wavelengths.

In another further aspect, additional metrology targets are used in conjunction with the overlay targets described herein to reduce measurement sensitivity to structural asymmetries. In effect, measurement data collected from these additional metrology targets is used to de-correlate the effects of asymmetry on the overlay measurement.

In addition, methods and systems for creating an image-based measurement model based only on measured, image-based training data (e.g., images collected from a Design of Experiments (DOE) wafer) are presented. The trained, image-based measurement model is then used to calculate values of one or more parameters of interest directly from measured image data collected from other wafers. Typically, different measurement systems are used for metrology and inspection applications, however, the methods and systems described herein are applicable to both metrology and inspection applications.

In one aspect, the trained, image-based measurement models described herein receive image data directly as input and provide values of one or more parameters of interest as output. By streamlining the measurement process, the predictive results are improved along with a reduction in computation and user time.

In a further aspect, values of parameters of interest may be determined from images of on-device structures. In these embodiments, images of on-device structures are used to train an image-based measurement model as described herein. The trained, image-based measurement model is then used to calculate values of one or more parameters of interest directly from images of the same on-device structures collected from other wafers.

In another further aspect, metrology targets are used. In these embodiments, images of metrology target structures are used to train an image-based measurement model as described herein. The trained, image-based measurement model is then used to calculate values of one or more parameters of interest directly from images of the same metrology target structures collected from other wafers. If metrology targets are used, multiple targets can be measured from single image and the metrology target can include one structure or at least two different structures.

In yet another further aspect, measurement data derived from measurements performed by a combination of multiple, different measurement techniques is collected for model building, training, and measurement.

By using only raw image data to create the image-based measurement model, as described herein, the errors and approximations associated with traditional image based metrology methods are reduced. In addition, the image-based measurement model is not sensitive to systematic errors, asymmetries, etc. because the image-based measurement model is trained based on image data collected from a particular metrology system and used to perform measurements based on images collected from the same metrology system.

In general, the methods and systems described herein analyze each image as a whole. Instead of recognizing individual features in the image, each pixel is considered as an individual signal containing information about (or sensitive to) structural parameters, process parameters, dispersion parameters, etc.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for measuring overlay error between structures formed on a substrate by successive lithographic processes are presented herein. Overlay error is measured based on zero order scatterometry signals. In one aspect, only two overlay targets are employed to perform an overlay measurement. Scatterometry data is collected from each target at two different azimuth angles to produce symmetric signals. The symmetric signals are used to determine overlay error.

Figure 1:
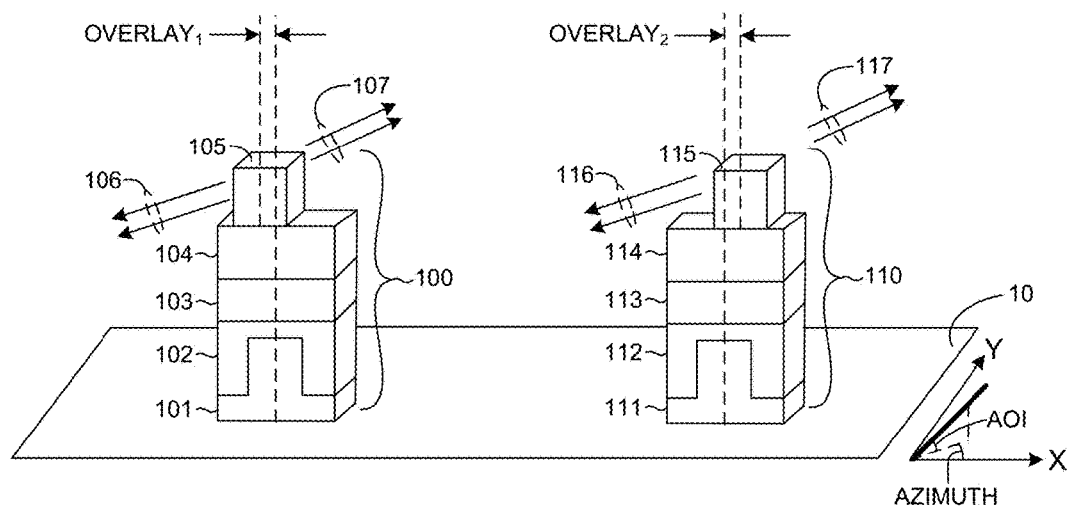
FIG. 1 depicts overlay targets 100 and 110 disposed on a specimen 10 under measurement.

FIG. 1 depicts overlay targets 100 and 110 disposed on a specimen 10 under measurement. Overlay target 100 includes two grating structures 101 and 105 offset from one another by an overlay distance, $OVERLAY_1$. In the embodiment depicted in FIG. 1, grating structure 105 is disposed on a top layer (i.e., exposed) and grating structure 101 is disposed in a layer beneath the top layer (i.e., buried). Intervening layers 102-104 separate grating structure 101 from grating structure 105. Similarly, overlay target 110 includes two grating structures 111 and 115 offset from one another by an overlay distance, $OVERLAY_2$. In the embodiment depicted in FIG. 1, grating structure 115 is disposed on a top layer (i.e., exposed) and grating structure 111 is disposed in a layer beneath the top layer (i.e., buried). Intervening layers 112-114 separate grating structure 111 from grating structure 115.

In one aspect, overlay targets 100 and 110 each include a programmed overlay offset in a direction opposite one another. As depicted in FIG. 1, grating structure 105 is offset with respect to grating structure 101 by a total overlay distance, $OVERLAY_1$. This distance includes a programmed overlay distance, d, and the overlay distance to be measured. As depicted in FIG. 1, the programmed overlay extends in the −X direction. Thus, the actual overlay $OVERLAY_1$, between grating structure 105 and grating structure 101 is described with reference to equation (1).

$$OVERLAY_1 = OVERLAY - d \quad (1)$$

Grating structure 115 is offset with respect to grating structure 111 by a total overlay distance, $OVERLAY_2$. This distance includes a programmed overlay distance, d, and the overlay distance to be measured. As depicted in FIG. 1, the programmed overlay extends in the +X direction, opposite that of overlay target 100. Thus, the actual overlay, $OVERLAY_2$, between grating structure 115 and grating structure 111 is described with reference to equation (2).

$$OVERLAY_2 = OVERLAY + d \quad (2)$$

Figure 4:
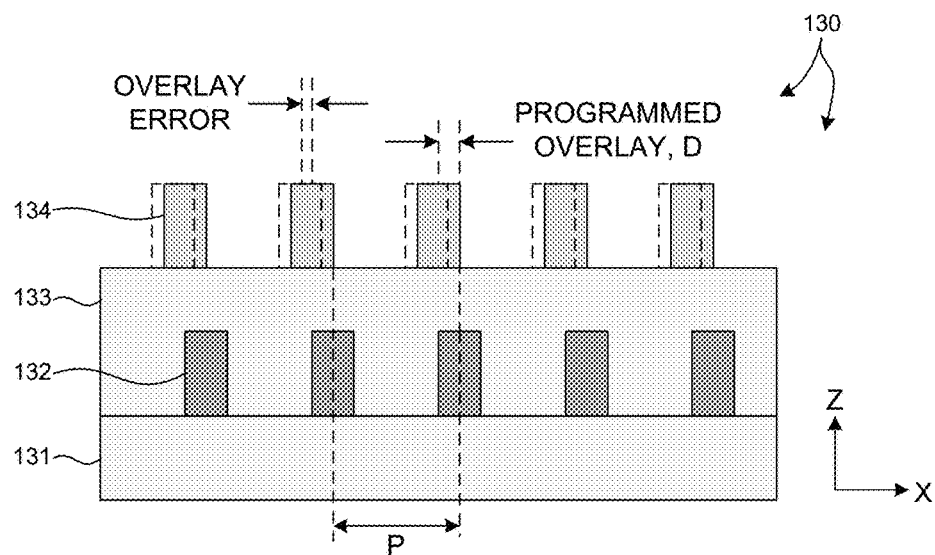
FIG. 4 illustrates a multi-layer, line/space metrology target 130.

FIG. 4 depicts a multi-layer overlay target 130 that includes a substrate 131, a grating structure 132, a fill layer 133, and another grating structure 134 that is spatially offset in the x-direction from the first patterned structure 132. The pitch of both patterned structures 132 and 134 is a distance, P. In most cases, sensitivity to overlay error is at its minimum when there is no overlay. In the depicted embodiment, the patterned structure 134 is offset from patterned structure 132 by a programmed overlay offset distance, d, to increase measurement sensitivity. In the embodiment depicted in FIG. 4, overlay error is the displacement of the patterned structure 134 relative to its programmed overlay offset.

A variety of different metrology targets may be contemplated within the scope of this invention. In some embodiments, the metrology targets are based on conventional line/space targets. In some other embodiments, the metrology targets are device-like structures. In some other embodiments, the metrology targets are the actual devices themselves, thus no specialized metrology target is employed. Regardless of the type of metrology target employed, a set of overlay targets having offsets in opposite directions must be provided to perform overlay measurements with two targets as described herein.

In some examples, the overlay targets are located in a scribeline of a production wafer. In some other examples, the overlay targets are located in the active die area. In some embodiments, the measurements are performed in a periodic area of an actual device, e.g., in a 10 mm by 10 mm area using small spot SE.

Figure 5:
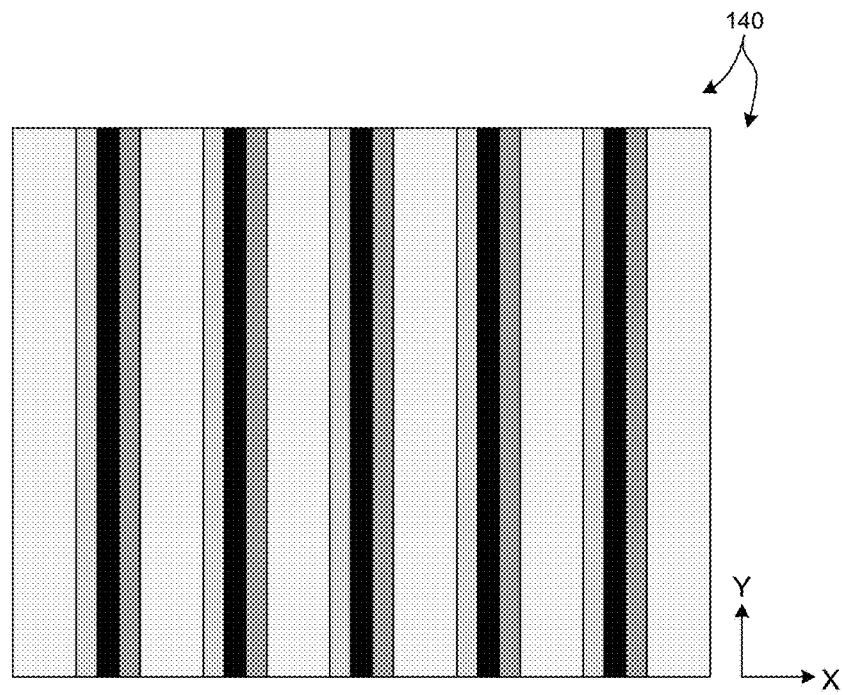
FIG. 5 illustrates a multi-layer, line/space metrology target 140 having two grating structures offset in the x-direction.
Figure 6:
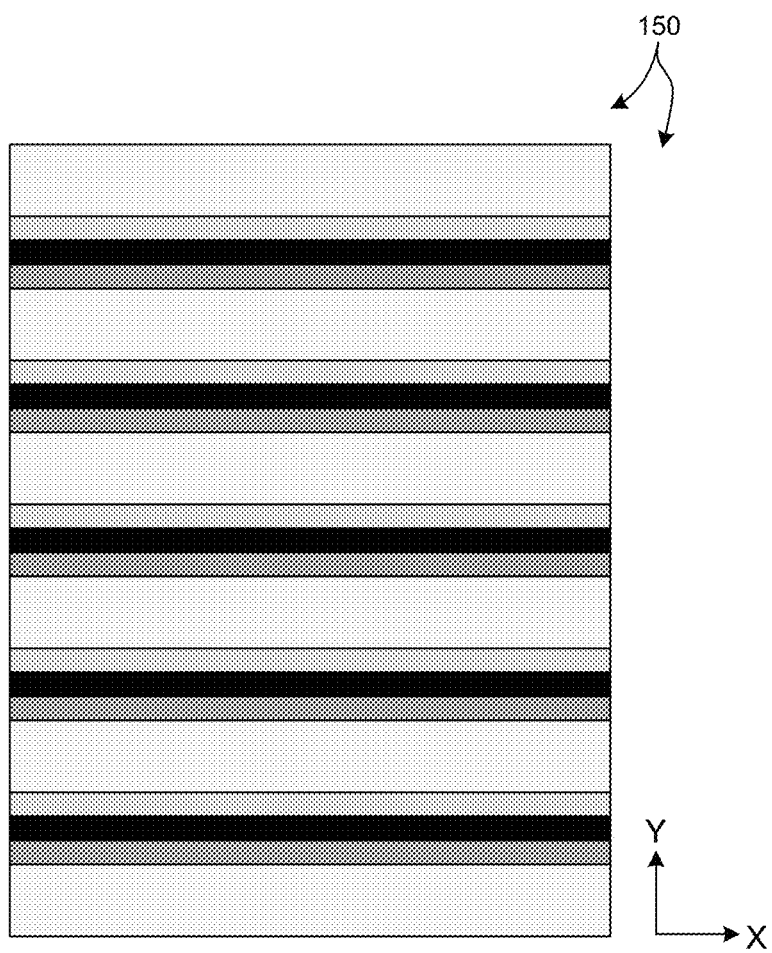
FIG. 6 illustrates a multi-layer, line/space metrology target 150 having two grating structures offset in the y-direction.

In some embodiments, grating targets are provided that have offset patterns in both the x and y directions. For example, FIG. 5 depicts an overlay target 140 having two offset grating structures as described with reference to FIG. 4. In the embodiment depicted in FIG. 5, the grating structures are offset in the x-direction. FIG. 6 depicts an overlay target 150 having two offset grating structures as described with reference to FIG. 4. In the embodiment depicted in FIG. 6, the grating structures are offset in the y-direction.

In some embodiments, multiple, different targets offset in opposite and orthogonal directions are employed in each die. This may be advantageous to minimize the effects of underlayers on measurement accuracy.

In a further aspect, scatterometry signals (e.g., spectra) are collected from overlay targets 100 and 110 at two different azimuth angles. In the embodiment depicted in FIG. 1, scatterometry signals 106 are collected from overlay target 100 at an azimuth angle of 45 degrees and scatterometry signals 107 are collected from overlay target 100 at an azimuth angle of 225 degrees. Similarly, scatterometry signals 116 are collected from overlay target 110 at an azimuth angle of 45 degrees and scatterometry signals 117 are collected from overlay target 110 at an azimuth angle of 225 degrees.

Figure 8:
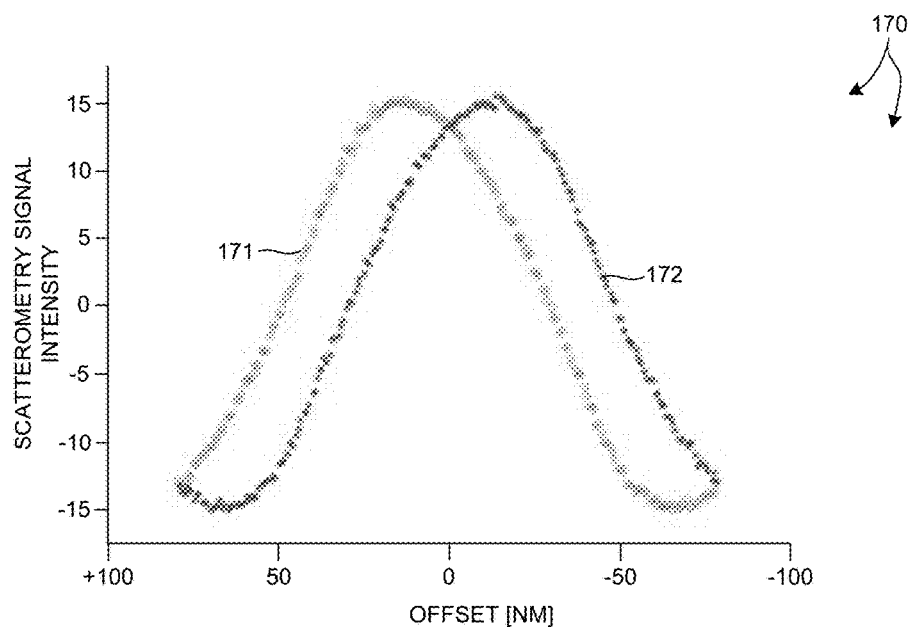
FIG. 8 depicts a plot 170 including collected scatterometry signals 171 associated with measurements of overlay target 100 at an azimuth angle of 225 degrees and scatterometry signals 172 associated with measurements of overlay target 100 at an azimuth angle of 45 degrees.
Figure 9:
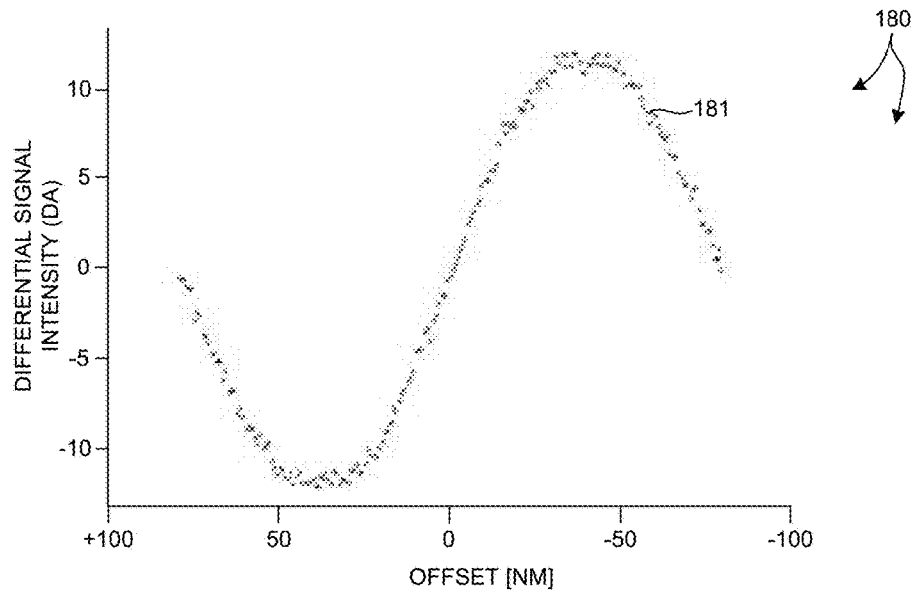
FIG. 9 depicts a plot 180 of a differential signal 181 derived from scatterometry signals 172 and scatterometry signals 171.

FIG. 8 depicts a plot 170 including collected scatterometry signals 171 associated with measurements of overlay target 100 at an azimuth angle of 225 degrees and scatterometry signals 172 associated with measurements of overlay target 100 at an azimuth angle of 45 degrees. FIG. 9 depicts a plot 180 of a differential signal 181 that is simply the difference between scatterometry signals 172 and scatterometry signals 171. As illustrated in FIG. 8, the scatterometry signals from a particular target collected at azimuth angles of 45° and 225° symmetric. As illustrated in FIG. 9, the difference between these signals approximates a sinusoidal waveform. In the region around the center of the waveform, the differential signal is approximately linear. Assuming a small process window, overlay is estimated by two points in the linear region. These two points (e.g., two different differential signals) are derived from data collected from two different targets, each having a different programmed overlay offset (e.g., overlay targets 100 and 110). In the embodiment described with reference to FIG. 1, overlay target 100 includes a programmed offset, d, in a direction opposite that of the same programmed offset, d, of overlay target 110. Differential signal, DA, is calculated from scatterometry signals 106 and 107, as described with reference to FIGS. 8 and 9. Similarly, differential signal, DB, is calculated from scatterometry signals 116 and 117. Based on the differential signals, DA and DB, associated with overlay targets 100 and 110, respectively, the unknown overlay is calculated as described by equation (3).

$$\text{OVERLAY} = d\left(\frac{DA + DB}{DA - DB}\right) \quad (3)$$

The measurement scenario described with reference to FIG. 1 and the resulting signals described with reference to FIGS. 8 and 9 are provided by way of non-limiting example. In general, offset distances may differ and the measurement response may be approximated by a general mathematical function. Similarly, the relationship between overlay and the differential signals may also be described by a general mathematical function.

In addition, the measurement scenario described with reference to FIG. 1 refers to offsets in one dimension (i.e., the x-direction). However, in general, overlay may be programmed in two dimensions (e.g., the x and y directions).

In the aforementioned example, the scatterometry signals collected from the overlay targets included a single wavelength. However, in general, scatterometry signals are collected over a range of different wavelengths to improve measurement sensitivity. In a further aspect, the overlay measurement technique described hereinbefore is applied to scatterometry signals including multiple wavelengths.

Figure 10:
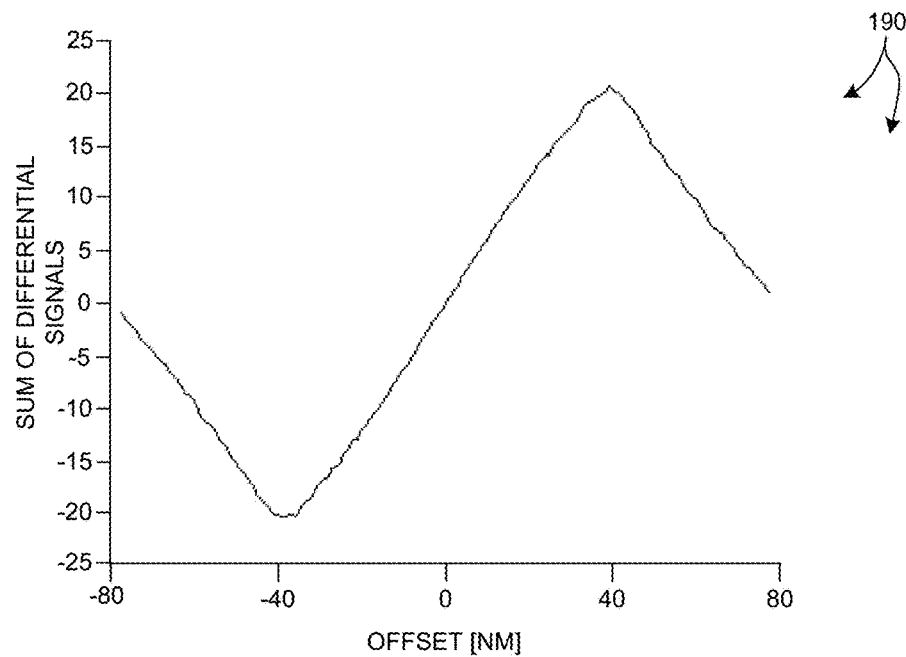
FIG. 10 depicts a plot 190 of a summed differential signal associated with measurements of overlay target 100 at 45 degree and 225 degree azimuth angles and multiple wavelengths.

In one example, differential signals are calculated at each wavelength as described hereinbefore and the resulting differential signals are summed to arrive at summed differential signals associated with each overlay target. The summed differential signals are used to calculate the unknown overlay as described by equation (3), where DA and DB are summed differential signals associated with two targets. FIG. 10 depicts a plot 190 of a summed differential signal associated with measurements of overlay target 100 at 45 degree and 225 degree azimuth angles and multiple wavelengths.

In another example, the differential signals are calculated at different wavelengths as described hereinbefore and the resulting differential signals are summed with different weights on different wavelengths. In one example, the weights are determined based on a linear fit of principal components of differential signals for a set of targets having a known overlay to a sinusoidal function.

Figure 7:
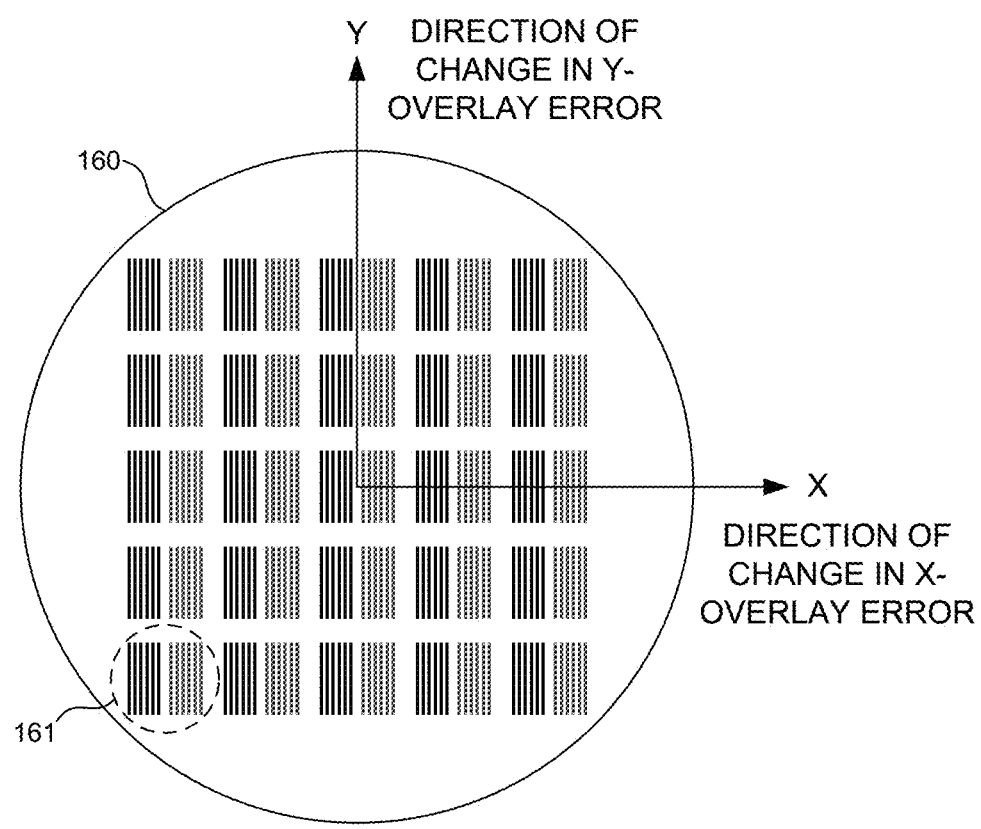
FIG. 7 illustrates a DOE wafer 160 having a grid of targets that exhibit known variations in overlay error in one embodiment.

In some embodiments, variations of overlay are organized in a Design of Experiments (DOE) pattern on the surface of a semiconductor wafer (e.g., DOE wafer). In this manner, the measurement sites interrogate different locations on the wafer surface that correspond with different overlay values. In one example, the DOE pattern is an overlay error pattern. Typically, a DOE wafer exhibiting an overlay error pattern includes a grid pattern of measurement sites. In one grid direction (e.g., the x-direction), the overlay is varied in the x-direction while the overlay in the y-direction is held constant. In the orthogonal grid direction (e.g., the y-direction), the overlay error in the y-direction is varied while the overlay error in the x-direction is held constant. In this manner, scatterometry data collected from the DOE wafer includes data associated with known variations in the overlay in both the x and y directions. FIG. 7 depicts a DOE wafer 160 having a grid of targets (e.g., target 161) that exhibit known variations in overlay error. The x-direction overlay errors vary as a function of location on the DOE wafer 160 in the x-direction. The y-direction overlay errors vary as a function of location on the DOE wafer 160 in the y-direction. In some examples, the x and y overlay errors range from −20 nanometers to 20 nanometers. In some other examples, the x and y overlay errors range from −80 to 80 nanometers. In general, any overlay error range may be contemplated within the scope of this patent document.

Differential scatterometry signals are collected for each of the training targets in the DOE measurement set at each wavelength. A number of principal features are extracted from each set of differential signals based on a mathematical transformation. The transformation maps the original signals from the original measurement space to another mathematical domain where the measurement data can be accurately represented by a reduced set of signals (e.g., principal coordinates). The transformation itself is determined based on the variations in overlay in the training data. Each measured signal is treated as an original signal that changes for different overlay measurements in the set of training data. The transformation may be applied to all of the differential signals, or a subset of the differential signals. In some examples, the differential signals subject to analysis are chosen randomly. In some other examples, the differential signals subject to analysis are chosen due to their relatively high sensitivity to changes in overlay. For example, signals that are not sensitive to changes in overlay may be ignored.

By way of non-limiting example, the transformation may be achieved using any of a principal component analysis (PCA) model, a kernel PCA model, a non-linear PCA model, an independent component analysis (ICA) model or other dimensionality reduction methods using dictionaries, a discrete cosine transform (DCT) model, fast fourier transform (FFT) model, a wavelet model, etc.

For the given training data, principal components of the differential signals for the measured targets are used to fit a linear model to a sinusoidal function of overlay. The sinusoidal function has a period equal to the pitch of the grating target and zero phase as illustrated in equation (4).

$$\sin\left(\frac{2\pi}{P} \cdot \text{OVERLAY}\right) = a_0 + \sum_{i=1}^{N} a_i PC_i + \varepsilon \quad (4)$$

Figure 11:
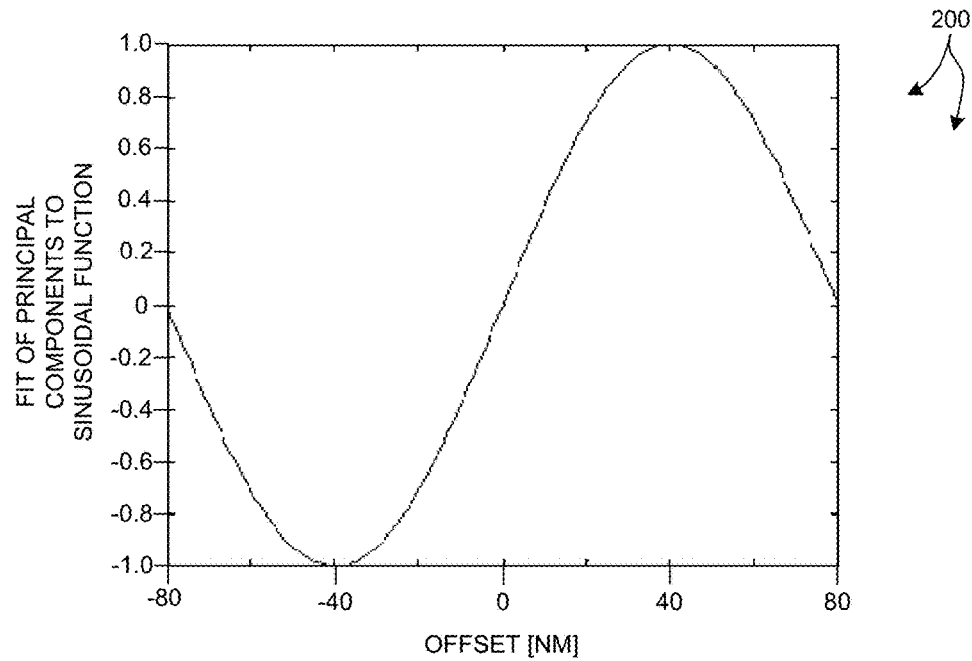
FIG. 11 depicts a plot 200 illustrating a sinusoid function fitted with principal components of differential signals associated with DOE measurements.

$PC_i$ are principal components, $\varepsilon$ is a zero mean Gaussian noise, and $a_i$ are linear model coefficients that are learned from the training data (i.e., the known overlay values). FIG. 11 depicts a plot 200 illustrating a sinusoid function fitted with principal components of differential signals associated with DOE measurements in accordance with equation (4). After fitting, overlay is calculated based on principal components of differential signals calculated at different wavelengths based on equation (5).

$$\text{OVERLAY} = \frac{P}{2\pi} \arcsin\left(a_0 + \sum_{i=1}^{N} a_i PC_i\right) \quad (5)$$

The sinusoidal model described hereinbefore is provided by way of non-limiting example. In general, offset distances may differ and the measurement response may be approximated by a general mathematical function. Similarly, the principal components may be fit to any suitable mathematical function.

In many examples, the measurement of overlay is affected by non-overlay related asymmetries. Some of these asymmetries result from processes applied to the top or bottom gratings of the overlay targets. Structures located close to each other are affected similarly by the same process, and thus they share the same information about process induced variations in structure.

In a further aspect, additional metrology targets are used in conjunction with the overlay targets described herein to reduce measurement sensitivity to structural asymmetries. In effect, measurement data collected from these additional metrology targets is used to de-correlate the effects of asymmetry on the overlay measurement.

In one example, scatterometry data is collected from the overlay targets at different azimuth angles as described with reference to FIG. 1. However, in addition, scatterometry data is collected from an additional metrology target at the same azimuth angles. The metrology target does not include overlay information, but it does include a bottom grating structure that exhibits the same process induced asymmetry as the overlay targets.

Figure 12:
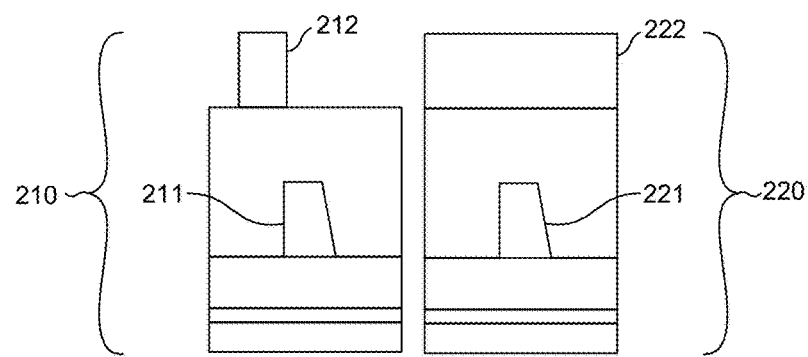
FIG. 12 depicts an overlay target 210 including a bottom grating feature 211 that includes a process induced asymmetry and a metrology target 220 disposed close to overlay target 210 that includes the same process induced asymmetry.

FIG. 12 depicts an overlay target 210 including a bottom grating feature 211 that includes a process induced asymmetry and a top grating feature 212. Overlay target 210 is one of the overlay targets involved in a two-target differential measurement as described with reference to FIG. 1. In the example depicted in FIG. 12 a metrology target 220 is disposed close to overlay target 210, and is thus subjected to similar process induced variations. Metrology target 220 includes a bottom grating feature 221 that has the same process induced asymmetry as the bottom grating feature 211 of overlay target 210. However, layer 222 of metrology target 220 does not include a top grating structure. Thus, metrology target 220 does not include any overlay information.

Process induced variations that induce structural asymmetry are organized in a Design of Experiments (DOE) pattern on the surface of one or more semiconductor wafers (e.g., DOE wafers). In this manner, the measurement sites interrogate different locations on the wafer surface that correspond with different process parameter values.

Scatterometry signals are collected at the various measurement sites for each of the metrology targets (e.g., metrology target 220) and each of the overlay targets in the DOE measurement set at each azimuth angle. A number of principal features are extracted from each set of scatterometry signals based on a mathematical transformation. The transformation maps the original signals, $S(M_1)$, from the metrology targets in the original measurement space to another mathematical domain, $S'(M_1)$, where the measurement data is accurately represented by a reduced set of signals (e.g., principal coordinates). The transformation, $F_1$, maps the original measurements of the metrology targets to a set of principal components as illustrated in equation (6).

$$F_1:S(M_1) \rightarrow S'(M_1) \tag{6}$$

The same transformation, $F_1$, is used to map the original signals, $S(O)$, from one or more of the overlay targets in the original measurement space to the same mathematical domain, $S'(O)$. The transformation, $F_1$, maps the original measurements of the metrology targets to a set of principal components as illustrated in equation (7).

$$F_1:S(O) \rightarrow S'(O) \tag{7}$$

Principal components of the metrology target, $S'(M_1)$, are fit to the signals of the overlay target, $S'(O)$, by a linear regression. This effectively subtracts common information shared among targets, namely process induced asymmetries. The remaining residual information, $S^*(O)$, includes the overlay error information that is not shared among the targets. Equation (8) illustrates the linear fit of the scatterometry signals of the metrology target to the signals of the overlay target.

$$S^*_i(O) = S'_i(O) - a_i S'_i(M_1) + \varepsilon_i \tag{8}$$

As a result, $S^*(O)$, includes information about overlay while effects of under-layer variations including asymmetry of the bottom grating are reduced. The resulting overlay signals, $S^*(O)$, for each azimuth angle are used to calculate the differential signals as described hereinbefore.

In another example, scatterometry data is collected from the overlay targets at different azimuth angles as described with reference to FIG. 1. However, in addition, scatterometry data is collected from an additional metrology target at the same azimuth angles. The metrology target does not include overlay information, but it does include a top grating structure that exhibits the same process induced asymmetry as the overlay targets.

Figure 13:
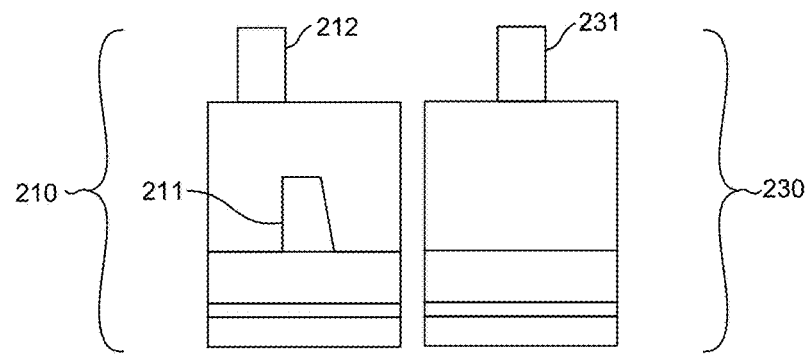
FIG. 13 depicts an overlay target 210 including a a top grating feature 212 that includes a process induced asymmetry and a metrology target 230 disposed close to overlay target 210 that includes the same process induced asymmetry.

FIG. 13 depicts an overlay target 210 including a bottom grating feature 211 and a top grating feature 212 that includes a process induced asymmetry. Overlay target 210 is one of the overlay targets involved in a two-target differential measurement as described with reference to FIG. 1. In the example depicted in FIG. 13 a metrology target 230 is disposed close to overlay target 210, and is thus subjected to similar process induced variations. Metrology target 230 includes a top grating feature 231 that has the same process induced asymmetry as the top grating feature 212 of overlay target 210. However, metrology target 220 does not include any overlay information.

Process induced variations that induce structural asymmetry are organized in a Design of Experiments (DOE) pattern on the surface of one or more semiconductor wafers (e.g., DOE wafers). In this manner, the measurement sites interrogate different locations on the wafer surface that correspond with different process parameter values.

Scatterometry signals are collected at the various measurement sites for each of the metrology targets (e.g., metrology target 220) and the overlay targets in the DOE measurement set at each azimuth angle. A number of principal features are extracted from each set of scatterometry signals based on a mathematical transformation. The transformation maps the original signals, $S(M_2)$, from the metrology targets in the original measurement space to another mathematical domain, $S'(M_2)$, where the measurement data is accurately represented by a reduced set of signals (e.g., principal coordinates). The transformation, $F_2$, maps the original measurements of the metrology targets to a set of principal components as illustrated in equation (9).

$$F_2:S(M_2) \rightarrow S'(M_2) \tag{9}$$

The same transformation, $F_2$, is used to map the original signals, $S(O)$, from one or more of the overlay targets in the original measurement space to the same mathematical domain, $S'(O)$. The transformation, $F_2$, maps the original measurements of the metrology targets to a set of principal components as illustrated in equation (10).

$$F_2: S(O) \rightarrow S'(O) \tag{10}$$

Principal components of the metrology target, $S'(M_2)$, are fit to the signals of the overlay target, $S'(O)$, by a linear regression. This effectively subtracts common information shared among targets, namely process induced asymmetries. The remaining residual information, $S^*(O)$, includes the overlay error information that is not shared among the targets. Equation (11) illustrates the linear fit of the scatterometry signals of the metrology target to the signals of the overlay target.

$$S^*_i(O) = S'_i(O) - a_t S'_i(M_2) + \varepsilon_i \quad (11)$$

As a result, $S^*(O)$, includes information about overlay while effects of under-layer variations including asymmetry of the top grating are reduced. The resulting overlay signals, $S^*(O)$, for each azimuth angle are used to calculate the differential signals as described hereinbefore.

In yet another example, scatterometry data is collected from the overlay targets at different azimuth angles as described with reference to FIG. 1. However, in addition, scatterometry data is collected from two additional metrology targets at the same azimuth angles. The metrology targets do not include overlay information, but they include a top grating structure and a bottom grating structure, respectively, that exhibits the same process induced asymmetry as the overlay targets.

In this manner, one metrology target shares information about bottom grating asymmetry with the overlay target, and the other metrology target shares information about top grating asymmetry with the overlay target. Moreover, all three targets share information about other process induced variations.

Figure 14:
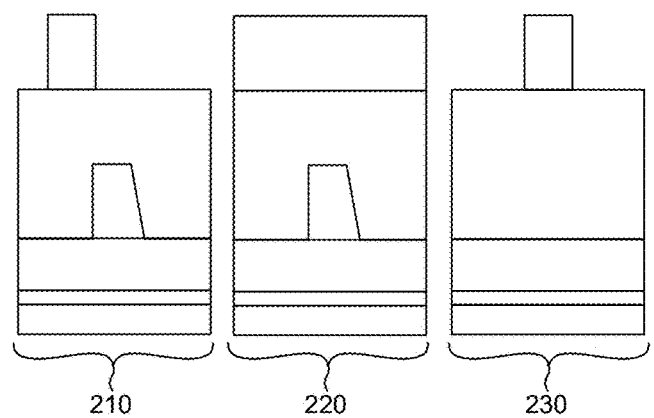
FIG. 14 depicts overlay target 210 and metrology targets 220 and 230 disposed close to overlay target 210.

FIG. 14 depicts overlay target 210 including a bottom grating feature 211 and a top grating feature 212 having process induced asymmetry as described hereinbefore. In the example depicted in FIG. 14 metrology targets 220 and 230 are disposed close to overlay target 210, and are thus subjected to similar process induced variations. Metrology target 220 includes a bottom grating feature that has the same process induced asymmetry as the bottom grating feature overlay target 210. Metrology target 230 includes a top grating feature that has the same process induced asymmetry as the top grating feature of overlay target 210. However, neither metrology target includes any overlay information. In this example, the asymmetry reduction calculations described with respect to FIGS. 12 and 13 can be applied in any order, or together, to arrive at overlay signals having reduced process induced asymmetry for each azimuth angle. These signals are subsequently used to calculate differential signals and overlay as described hereinbefore.

In a further aspect, the methods and systems for estimating overlay based on multiple wavelengths and with reduced sensitivity to process induced asymmetry are combined to improve overlay measurement accuracy.

Figure 3:
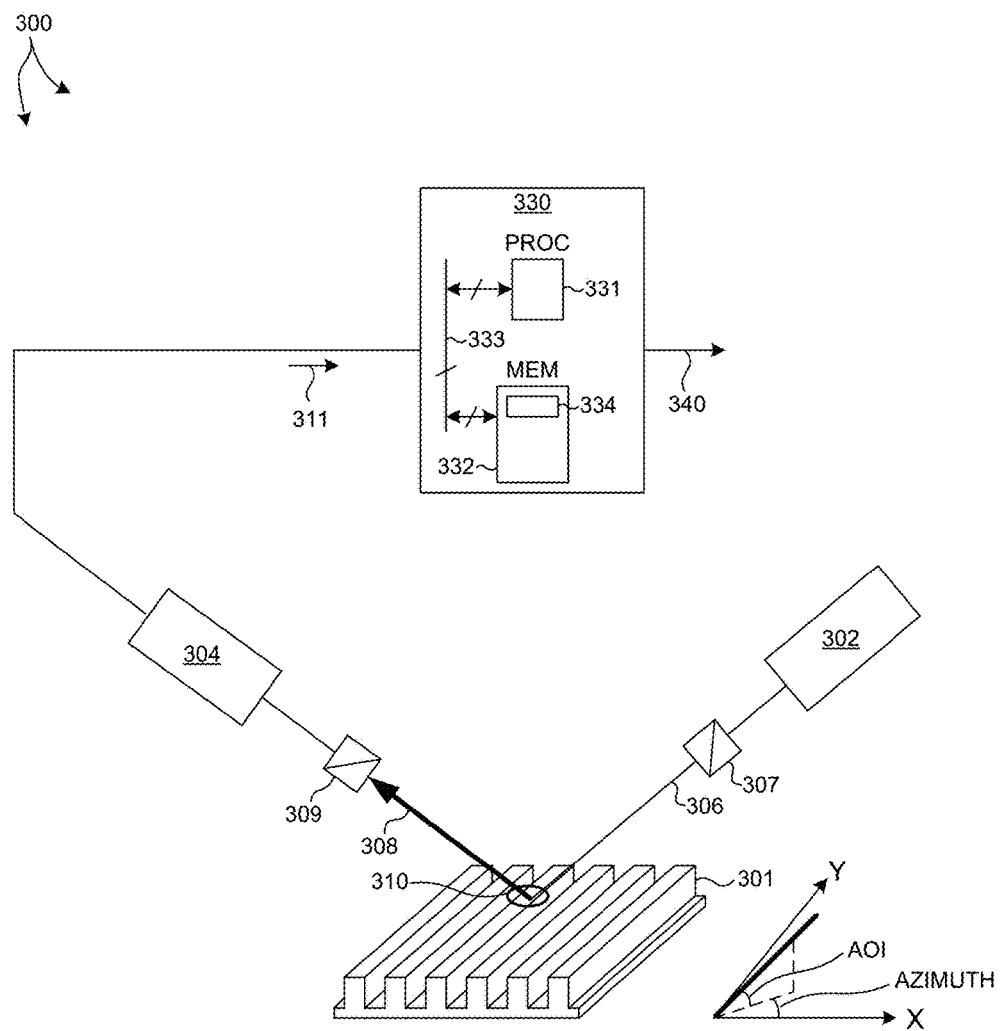
FIG. 3 illustrates a system 300 for estimating overlay from signals collected from a specimen in accordance with exemplary method 120 presented herein.

FIG. 3 illustrates a system 300 for measuring characteristics of a specimen in accordance with the exemplary methods presented herein. As shown in FIG. 3, the system 300 may be used to perform spectroscopic ellipsometry measurements of one or more structures of a specimen 301. In this aspect, the system 300 may include a spectroscopic ellipsometer equipped with an illuminator 302 and a spectrometer 304. The illuminator 302 of the system 300 is configured to generate and direct illumination of a selected wavelength range (e.g., 100-2500 nm) to the structure disposed on the surface of the specimen 301. In turn, the spectrometer 304 is configured to receive illumination reflected from the surface of the specimen 301. It is further noted that the light emerging from the illuminator 302 is polarized using a polarization state generator 307 to produce a polarized illumination beam 306. The radiation reflected by the structure disposed on the specimen 301 is passed through a polarization state analyzer 309 and to the spectrometer 304. The radiation received by the spectrometer 304 in the collection beam 308 is analyzed with regard to polarization state, allowing for spectral analysis by the spectrometer of radiation passed by the analyzer. These spectra 311 are passed to the computing system 330 for analysis of the structure.

As depicted in FIG. 3, system 300 includes a single measurement technology (i.e., SE). However, in general, system 300 may include any number of different measurement technologies. By way of non-limiting example, system 300 may be configured as a spectroscopic ellipsometer (including Mueller matrix ellipsometry), a spectroscopic reflectometer, a spectroscopic scatterometer, an overlay scatterometer, an angular resolved beam profile reflectometer, a polarization resolved beam profile reflectometer, a beam profile reflectometer, a beam profile ellipsometer, any single or multiple wavelength ellipsometer, or any combination thereof. Furthermore, in general, measurement data collected by different measurement technologies and analyzed in accordance with the methods described herein may be collected from multiple tools, rather than one tool integrating multiple technologies.

In a further embodiment, system 300 may include one or more computing systems 330 employed to perform overlay measurements in accordance with the methods described herein. The one or more computing systems 330 may be communicatively coupled to the spectrometer 304. In one aspect, the one or more computing systems 330 are configured to receive measurement data 311 associated with measurements of the structure of specimen 301.

It should be recognized that the various steps described throughout the present disclosure may be carried out by a single computer system 330 or, alternatively, a multiple computer system 330. Moreover, different subsystems of the system 300, such as the spectroscopic ellipsometer 304, may include a computer system suitable for carrying out at least a portion of the steps described herein. Therefore, the aforementioned description should not be interpreted as a limitation on the present invention but merely an illustration. Further, the one or more computing systems 330 may be configured to perform any other step(s) of any of the method embodiments described herein.

In addition, the computer system 330 may be communicatively coupled to the spectrometer 304 in any manner known in the art. For example, the one or more computing systems 330 may be coupled to computing systems associated with the spectrometer 304. In another example, the spectrometer 304 may be controlled directly by a single computer system coupled to computer system 330.

The computer system 330 of the metrology system 300 may be configured to receive and/or acquire data or information from the subsystems of the system (e.g., spectrometer 304 and the like) by a transmission medium that may include wireline and/or wireless portions. In this manner, the transmission medium may serve as a data link between the computer system 330 and other subsystems of the system 300.

Computer system 330 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 330 and other systems (e.g., memory on-board metrology system 300, external memory, or other external systems). For example, the computing system 330 may be configured to receive measurement data from a storage medium (i.e., memory 332 or an external memory) via a data link. For instance, spectral results obtained using spectrometer 304 may be stored in a permanent or semi-permanent memory device (e.g., memory 332 or an external memory). In this regard, the spectral results may be imported from on-board memory or from an external memory system. Moreover, the computer system 330 may send data to other systems via a transmission medium. For instance, overlay values determined by computer system 330 may be communicated and stored in an external memory. In this regard, measurement results may be exported to another system.

Computing system 330 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 334 implementing methods such as those described herein may be transmitted over a transmission medium such as a wire, cable, or wireless transmission link. For example, as illustrated in FIG. 3, program instructions 334 stored in memory 332 are transmitted to processor 331 over bus 333. Program instructions 334 are stored in a computer readable medium (e.g., memory 332). Exemplary computer-readable media include read-only memory, a random access memory, a magnetic or optical disk, or a magnetic tape.

Figure 2:
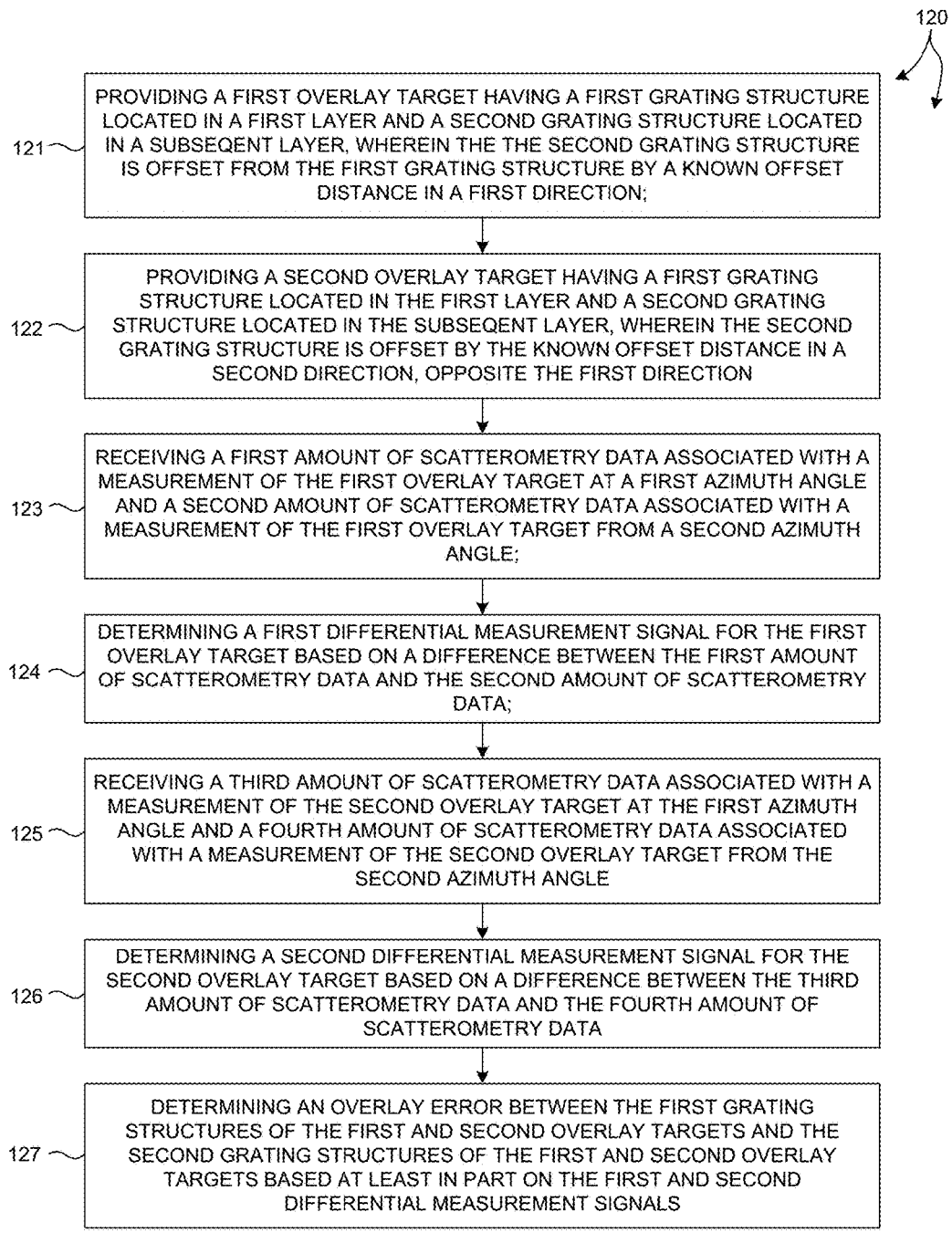
FIG. 2 is a flowchart illustrative of a method 120 of measuring overlay as described herein.

FIG. 2 illustrates a method 120 suitable for implementation by a metrology system such as metrology system 300 illustrated in FIG. 3 of the present invention. In one aspect, it is recognized that data processing blocks of method 120 may be carried out via a pre-programmed algorithm executed by one or more processors of computing system 330, or any other general purpose computing system. It is recognized herein that the particular structural aspects of metrology system 300 do not represent limitations and should be interpreted as illustrative only.

In block 121, a first overlay target having a first grating structure located in a first layer and a second grating structure located in a subsequent layer is provided to metrology system 300. The second grating structure is offset from the first grating structure by a known offset distance in a first direction.

In block 122, a second overlay target having a first grating structure located in the first layer and a second grating structure located in the subsequent layer is provided to metrology system 300. The second grating structure is offset by the known offset distance in a second direction, opposite the first direction.

In block 123, a first amount of scatterometry data associated with a measurement of the first overlay target at a first azimuth angle and a second amount of scatterometry data associated with a measurement of the first overlay target from a second azimuth angle is received by computing system 330.

In block 124, a first differential measurement signal for the first overlay target is determined based on a difference between the first amount of scatterometry data and the second amount of scatterometry data.

In block 125, a third amount of scatterometry data associated with a measurement of the second overlay target at the first azimuth angle and a fourth amount of scatterometry data associated with a measurement of the second overlay target from the second azimuth angle is received by computing system 330.

In block 126, a second differential measurement signal for the second overlay target is determined based on a difference between the third amount of scatterometry data and the fourth amount of scatterometry data.

In block 127, an overlay error between the first grating structures of the first and second overlay targets and the second grating structures of the first and second overlay targets is determined based at least in part on the first and second differential measurement signals.

In another further aspect, measurement data derived from measurements performed by a combination of multiple, different measurement techniques is collected for overlay measurement. The use of measurement data associated with multiple, different measurement techniques increases the information content in the combined set of signals and reduces the overlay correlation to process or other parameters variations. Measurement data may be derived from measurements performed by any combination of multiple, different measurement techniques. In this manner, different measurement sites may be measured by multiple, different measurement techniques (e.g., optical SE, optical SR, 2D-BPR, etc.) to enhance the measurement information available for estimation of overlay error.

In general, any measurement technique, or combination of two or more measurement techniques may be contemplated within the scope of this patent document as the measurement data is in vector form. Because the techniques as described herein operate on vectors of data, it is possible to concatenate data from multiple, different metrologies, regardless of whether the data is two dimensional data, one dimensional data, or even single point data.

Exemplary measurement techniques that may provide data for analysis in accordance with the techniques described herein include, but are not limited to spectroscopic ellipsometry, including Mueller matrix ellipsometry, spectroscopic reflectometry, spectroscopic scatterometry, scatterometry overlay, beam profile reflectometry, both angle-resolved and polarization-resolved, beam profile ellipsometry, single or multiple discrete wavelength ellipsometry, transmission small angle x-ray scatterometer (TSAXS), small angle x-ray scattering (SAXS), grazing incidence small angle x-ray scattering (GISAXS), wide angle x-ray scattering (WAXS), x-ray reflectivity (XRR), x-ray diffraction (XRD), grazing incidence x-ray diffraction (GIXRD), high resolution x-ray diffraction (HRXRD), x-ray photoelectron spectroscopy (XPS), x-ray fluorescence (XRF), grazing incidence x-ray fluorescence (GIXRF), x-ray tomography, and x-ray ellipsometry. In general, any metrology technique applicable to the characterization of overlay of semiconductor structures, including image based metrology techniques, may be contemplated, individually, or in any combination.

In another further aspect, signals measured by multiple metrologies can be processed to reduce sensitivity to process variations and increase sensitivity to overlay. In some examples, signals from targets measured by different metrologies are subtracted from one another. In some other examples, signals from targets measured by different metrologies are fit to a model, and the residuals are used to estimate overlay as described herein. In one example, signals from a target measured by two different metrologies are subtracted to eliminate, or significantly reduce, the effect of process noise in each measurement result. In general, various mathematical operations can be applied between the signals measured by different metrologies to determine signals with reduced sensitivity to process variations and increased sensitivity to the parameters of interest.

In general, signals from multiple targets each measured by multiple metrology techniques increases the information content in the combined set of signals and reduces the overlay correlation to process or other parameters variations.

In another further aspect, the metrology system employed to perform overlay measurements as described herein (e.g., metrology system 300) includes an infrared optical measurement system. In these embodiments, the metrology system 300 an infrared light source (e.g., an arc lamp, an electrode-less lamp, a laser sustained plasma (LSP) source, or a supercontinuum source). An infrared supercontinuum laser source is preferred over a traditional lamp source because of the higher achievable power and brightness in the infrared region of the light spectrum. In some examples, the power provided by the supercontinuum laser enables measurements of overlay structures with opaque film layers.

A potential problem in overlay measurement is insufficient light penetration to the bottom grating. In many examples, there are non-transparent (i.e., opaque) film layers between the top and the bottom gratings. Examples of such opaque film layers include amorphous carbon, tungsten silicide (Wsix), tungsten, titanium nitride, amorphous silicon, and other metal and non-metal layers. Often, illumination light limited to wavelengths in the visible range and below (e.g., between 250 nm and 700 nm) does not penetrate to the bottom grating. However, illumination light in the infrared spectrum and above (e.g., greater than 700 nm) often penetrates opaque layers more effectively.

An operational definition of "opaque" in the ultra-violet and visible range is that the predicted precision for SCOL in the wavelength range of 250-700 nm is much worse than the required precision. This is due to attenuation of the propagating diffraction order carrying the relative position information between the first pattern and the second pattern. Measuring SCOL signals with illumination wavelengths greater than 700 nanometers (e.g., 800-1650 nm) improves SCOL precision when absorption is significantly less. In embodiments where illumination light having wavelengths greater than 700 nanometers is employed, the design pitch of the measurement target is selected such that there is usable SCOL signal.

Methods and systems for creating an image-based measurement model based only on measured, image-based training data (e.g., images collected from a Design of Experiments (DOE) wafer) are also presented herein. The trained, image-based measurement model is then used to calculate values of one or more parameters of interest directly from measured image data collected from other wafers. Typically, different measurement systems are used for metrology and inspection applications, however, the methods and systems described herein are applicable to both metrology and inspection applications.

In one aspect, the trained, image-based measurement models described herein receive image data directly as input and provide values of one or more parameters of interest as output. By streamlining the measurement process, the predictive results are improved along with a reduction in computation and user time.

In another aspect, values of parameters of interest may be determined from images of on-device structures. In some embodiments, images of on-device structures are used to train an image-based measurement model as described herein. The trained, image-based measurement model is then used to calculate values of one or more parameters of interest directly from images of the same on-device structures collected from other wafers. In these embodiments, the use of specialized targets is avoided. In some other embodiments, metrology targets are used and the target size can be less than 10 micron by 10 micron. If metrology targets are used, multiple targets can be measured from single image and the metrology target can include one structure or at least two different structures.

In some examples, the image-based measurement model can be created in less than an hour. In addition, by employing a simplified model, measurement time is reduced compared to existing image based metrology methods. Additional modeling details are described in U.S. Patent Publication No. 2014/0297211 and U.S. Patent Publication No. 2014/0316730, the subject matter of each are incorporated herein by reference in their entirety.

By using only raw image data to create the image-based measurement model, as described herein, the errors and approximations associated with traditional image based metrology methods are reduced. In addition, the image-based measurement model is not sensitive to systematic errors, asymmetries, etc. because the image-based measurement model is trained based on image data collected from a particular metrology system and used to perform measurements based on images collected from the same metrology system.

In general, the methods and systems described herein analyze each image as a whole. Instead of recognizing individual features in the image, each pixel is considered as an individual signal containing information about (or sensitive to) structural parameters, process parameters, dispersion parameters, etc.

Figure 15:
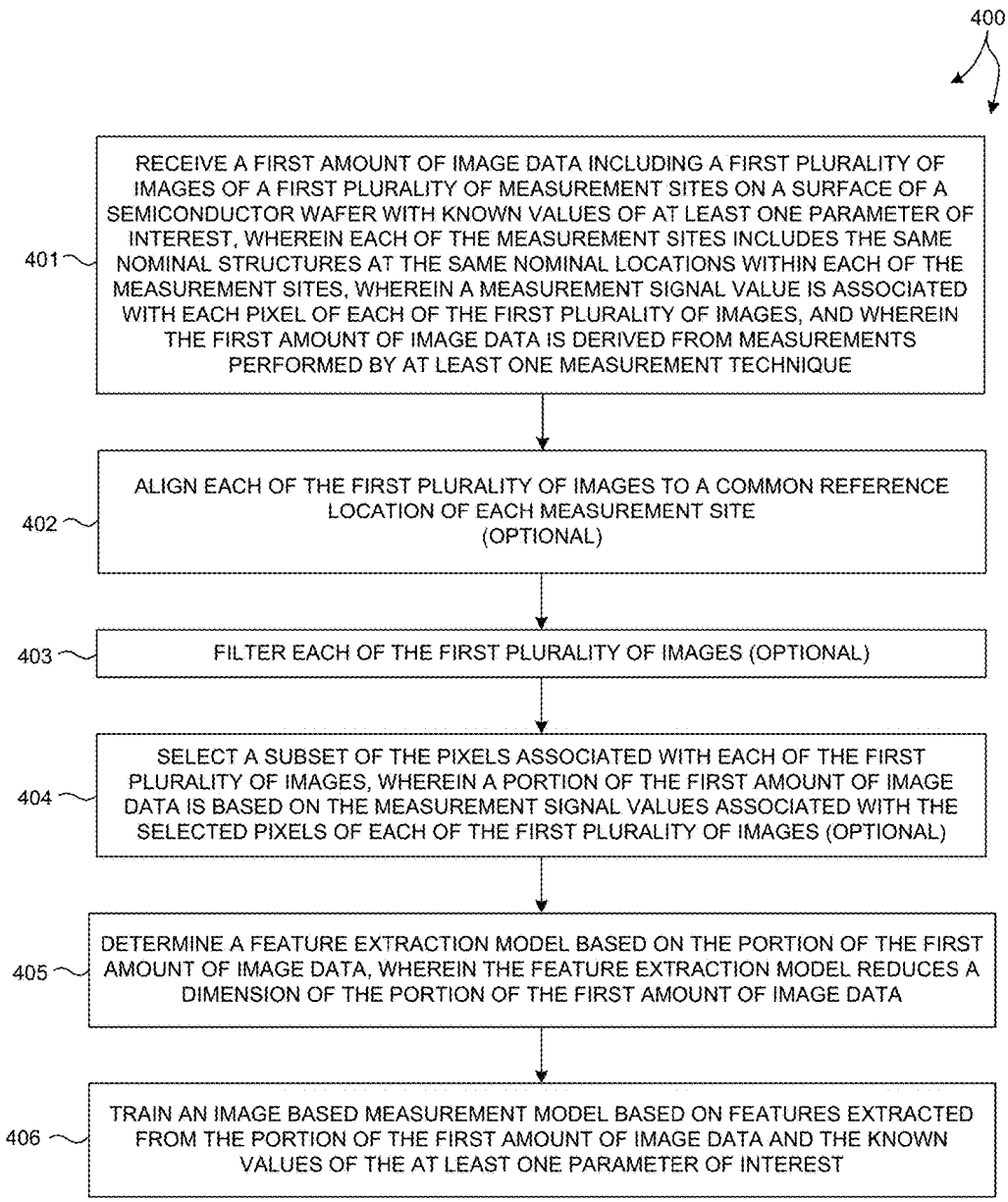
FIG. 15 is a flowchart illustrative of a method 400 of training an image based measurement model as described herein.
Figure 31:
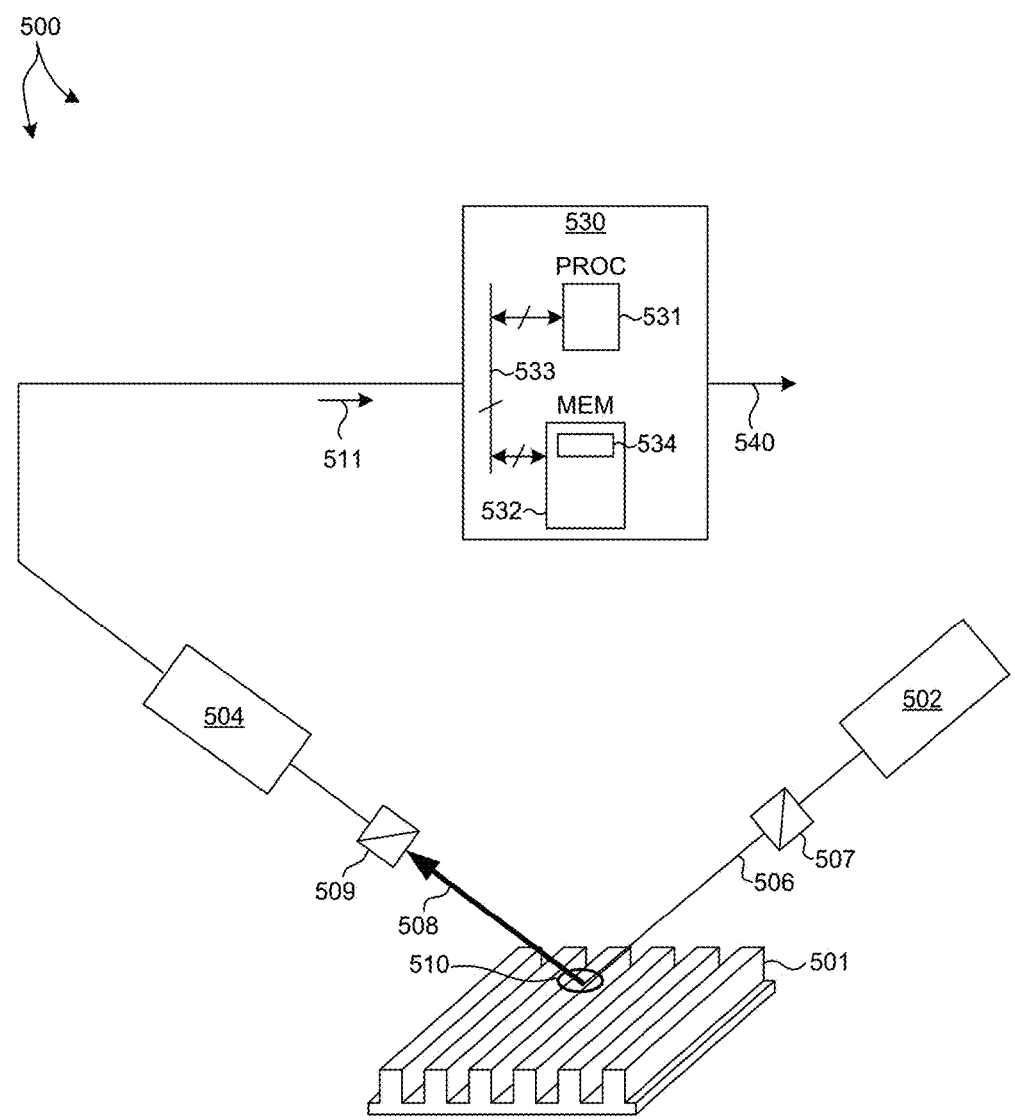
FIG. 31 illustrates a system 500 for performing image based measurements of parameters of interest in accordance with the exemplary methods 400 and 410 presented herein.

FIG. 15 illustrates a method 400 suitable for implementation by a measurement system such as measurement system 500 illustrated in FIG. 31 of the present invention. In one aspect, it is recognized that data processing blocks of method 400 may be carried out via a pre-programmed algorithm executed by one or more processors of computing system 530, or any other general purpose computing system. It is recognized herein that the particular structural aspects of measurement system 500 do not represent limitations and should be interpreted as illustrative only.

In block 401, a first amount of image data is received by computing system 530. The first amount of image data includes images of a number of measurement sites constructed on a surface of a specimen, such as a semiconductor wafer. Values of at least one parameter of interest of the specimen are known. In some examples, the parameter of interest is known based on measurements by a reference metrology system (e.g., CD-SEM, TEM, AFM, or other trusted metrology system). In examples where the image data is simulated, the parameter of interest is a known simulation parameter. In some examples, image data may be simulated using an electromagnetic simulation engine such as rigorous coupled wave analysis (RCWA). In some other examples, image data may be simulated using RCWA and a process simulator such as PROLITH®, available from KLA-Tencor Corporation, Milpitas, Calif. (USA).

The parameters of interest include one or more process parameters, structural parameters, dispersion parameters, or layout parameters. Each of the measurement sites includes the same nominal structures at the same nominal locations within each of the measurement sites. In one example, a measurement site encompasses a field area of a semiconductor wafer that is repeatedly constructed across the wafer surface. In some examples, a measurement site encompasses a die area that is repeatedly constructed across the wafer surface. Although, each measurement site nominally includes the same structures, in reality, and for purposes of model training, each measurement site includes variations of various parameters (e.g., CD, sidewall angle, height, overlay, etc.).

In some examples, the first amount of image data includes a single image of each measurement site. Each image of each measurement site includes a single measurement signal value associated with each pixel. In one example, the single measurement value is a reflectance at the location of each pixel measured by an imaging reflectometer at a particular set of measurement system settings (e.g., wavelength, polarization, angle of incidence, azimuth angle, etc.).

In some other examples, the first amount of image data includes multiple images of the same measurement site. Each of the images of each measurement site includes a single measurement signal value associated with each pixel. Thus, multiple measurement signal values are measured for each pixel. In general, each of the images of each measurement site is measured either by the same measurement system at different settings (e.g., wavelength, polarization, angle of incidence, azimuth angle, etc.), a different measurement technique, or a combination thereof. In this manner, a diverse set of measurement data may be assembled for each pixel of each measurement site. In general, image data can be collected from any imaging based system such as an optical imaging system, a microscope, a scanning electron microscope, a tunneling electron microscope, or other image forming systems.

Figure 17:
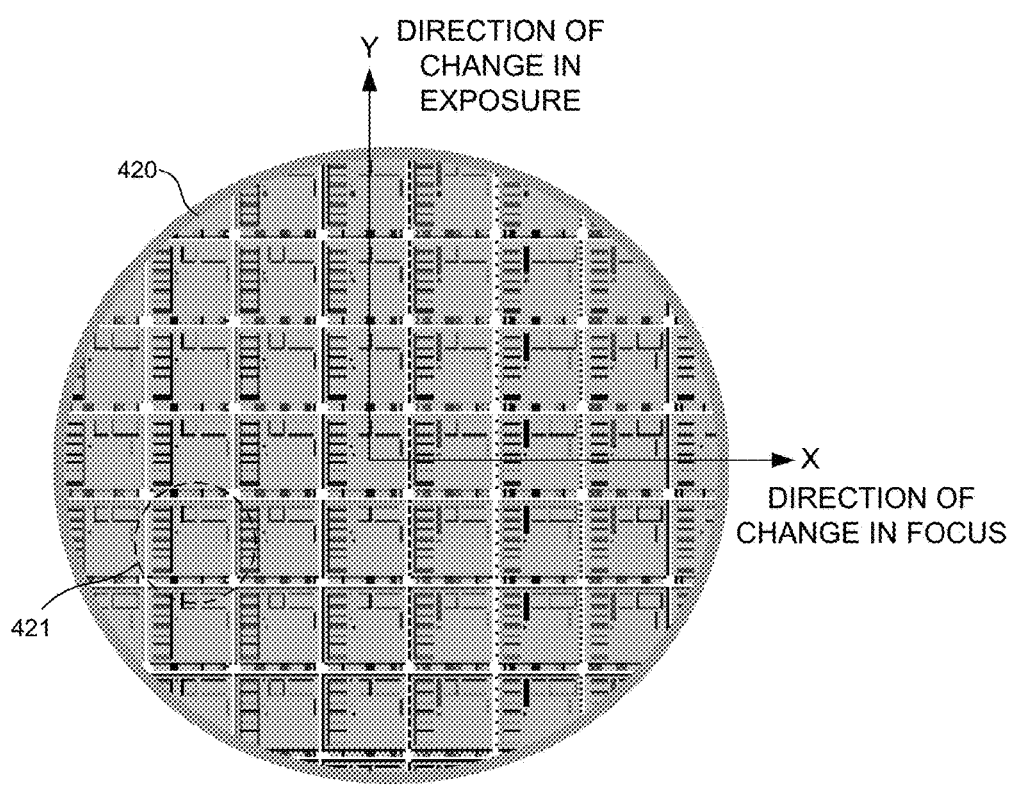
FIG. 17 depicts a design of experiments wafer 420 having a grid of measurement sites including structures that exhibit known variations of one or more parameters of interest.

For purposes of model training, variations of the parameter(s) of interest are organized in a Design of Experiments (DOE) pattern on the surface of a semiconductor wafer (e.g., DOE wafer). In this manner, the measurement sites interrogate different locations on the wafer surface that correspond with different values of the parameter(s) of interest. In one example, the DOE pattern is a focus exposure matrix (FEM) pattern. Typically, a DOE wafer exhibiting an FEM pattern includes a grid pattern of measurement sites. In one grid direction (e.g., the x-direction), the focus is varied while the exposure is held constant. In the orthogonal grid direction (e.g., the y-direction), the exposure is varied while the focus is held constant. In this manner, image data collected from the DOE wafer includes data associated with known variations in focus and exposure. FIG. 17 depicts a DOE wafer 420 having a grid of measurement sites (e.g., measurement site 421) including structures that exhibit known variations in the parameter(s) of interest (e.g., focus and exposure). The focus varies as a function of location on the DOE wafer 420 in the x-direction. The exposure varies as a function of location on the DOE wafer 420 in the y-direction.

Figure 18:
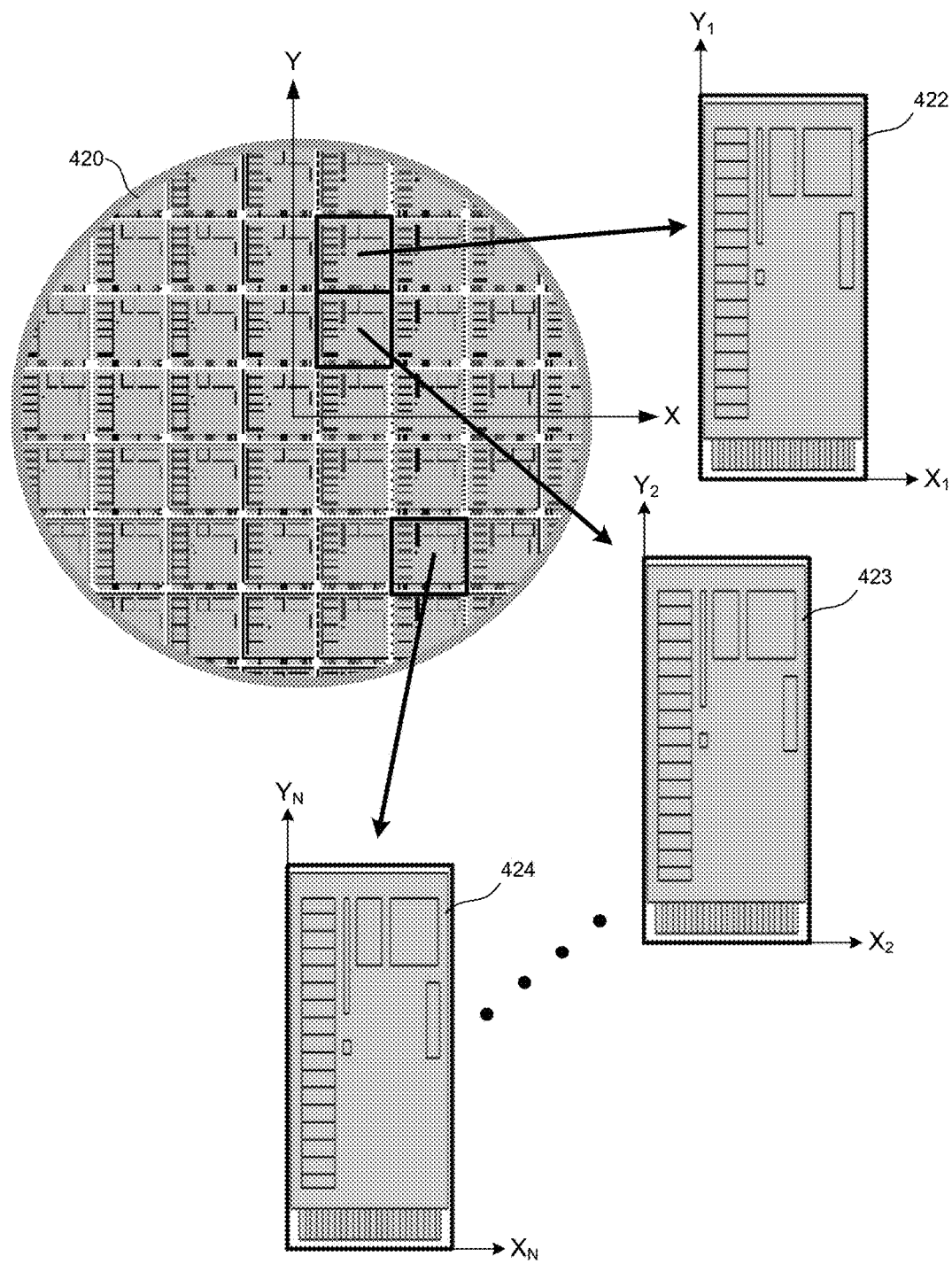
FIG. 18 depicts illustrative images 422-424 of different measurement sites of wafer 420.

In some embodiments, the images include device areas. Each pixel of a particular image of a measurement site represents the intensity of the collected light under specific illumination and collection conditions, wavelengths, polarization, etc. FIG. 18 depicts images 422-424 of different measurement sites of wafer 420. Each image represents an aerial view of the device structures within a measurement site. The measurement site is identified by its X and Y coordinates.

In some other embodiments, the images include specific targets designed to facilitate image-based measurement of the parameter(s) of interest. A specially designed target may be employed to improve device representation, maximize sensitivity to the parameter(s) of interest (focus, dose, CD), and reduce correlation to process variation.

Figure 25A:
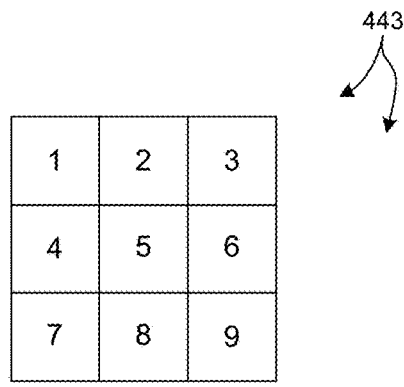
FIGS. 25A-25B exhibit a nine cell metrology target that may be advantageous for image-based measurement of parameters of interest.
Figure 25B:
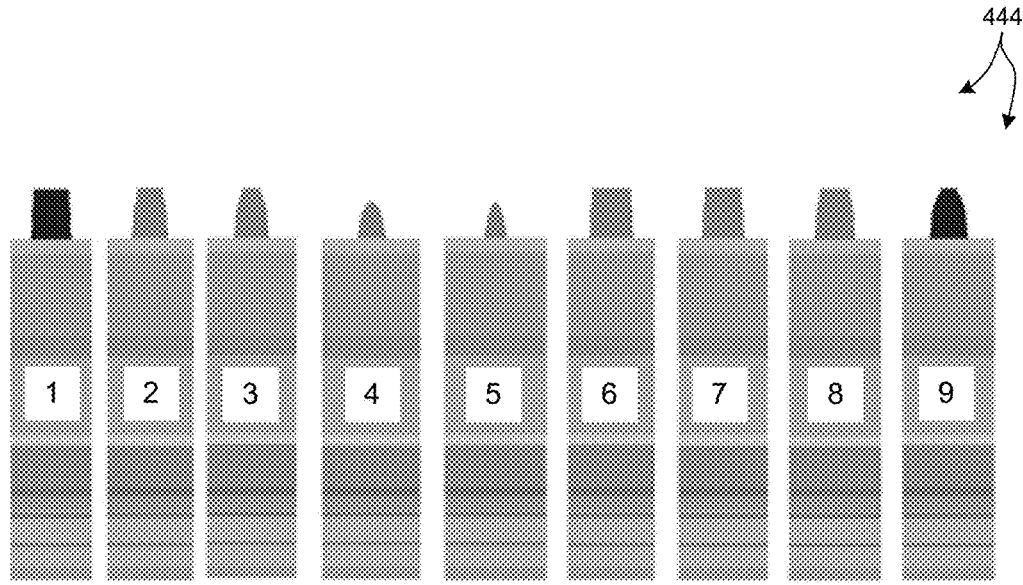

FIG. 25 depicts a top view of a nine cell target 443. A profile view 444 of each of the nine cells is depicted in FIG. 25B. The structures at each of the locations numbered 1 through 9 have different pitch/width combinations. In one example, the measured images include intensity (e.g., reflectance) values measured using three specific wavelengths (637 nm, 523 nm and 467 nm).

In the aforementioned example, the image data is associated with a DOE wafer processed with known variations in focus and exposure (i.e., dose). However, in general, image data associated with any known variation of process parameters, structural parameter, dispersion, etc., may be contemplated. The images of the DOE wafer should exhibit ranges of the parameter(s) of interest and should also exhibit ranges of other noise sources such as optical system errors (e.g., camera offset).

Figure 19:
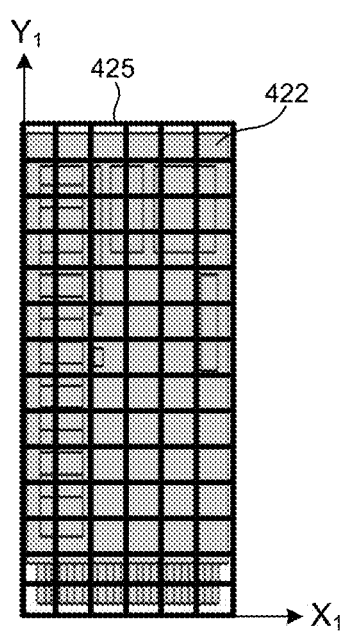
FIG. 19 illustrates a grid of pixels 425 associated with image 422.

In optional block 402, each of the first plurality of images is aligned with a common reference location of each measurement site. In this manner, any particular pixel from each image corresponds to the same location on each imaged measurement site. In one example, the collected images are aligned such that they match the first image of the set. FIG. 19 illustrates a grid of pixels 425 associated with image 422. In some examples, the measurement system operates at high precision and additional image alignment is not necessary. In this sense, block 402 is optional.

In optional block 403, each of the images received in block 101 is filtered by one or more image filters. Image filters may be employed for noise reduction, contrast enhancement, etc. In one example, image filters may be employed to reduce edge effects by detecting edges and removing or masking the edges and proximate regions. In this manner, subsequent image samples are taken from relatively homogenous device regions. The image filters employed may be selected by a user or by an automatic procedure. The number of different image filters and the parameters associated with each selected filter are chosen to improve the final measurement result without undue computational burden. Although, the use of image based filters may be advantageous, in general, it is not necessary. In this sense, block 403 is optional.

In optional block 404, a subset of the pixels associated with each of the first plurality of images is selected for model training and measurement. The measurement signal values associated with the same selected pixels of each of the first plurality of images are used for model training and measurement.

Figures 20, 21:
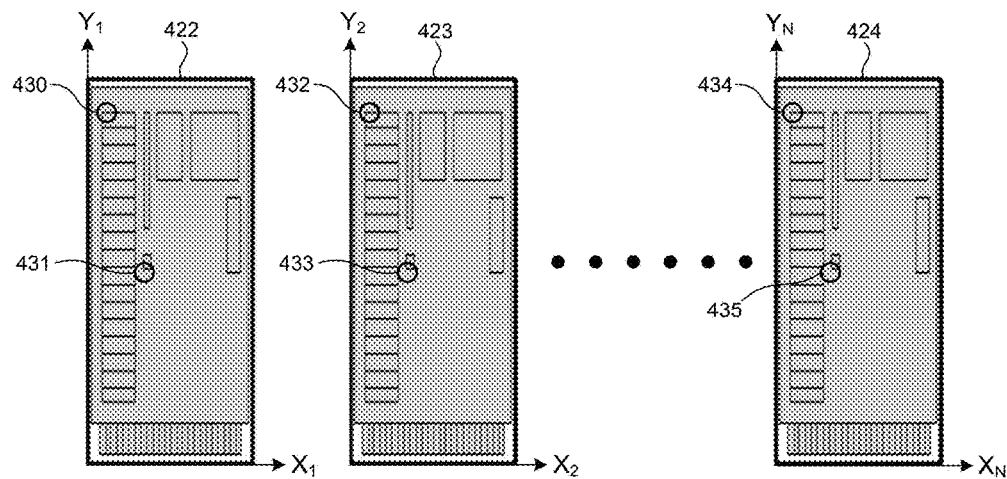
FIG. 20 depicts two different pixel locations selected for model training and measurement in accordance with method 400.
FIG. 21 depicts a vector 436 of measured intensity values sampled at the pixel locations illustrated in FIG. 20.

FIG. 20 depicts two different pixel locations selected for model training and measurement. In the depicted example, pixels 430, 432, and 434 correspond to the same location on images 422, 423, and 424, respectively. Similarly, pixels 431, 433, and 435 correspond to the same location on images 422, 423, and 424, respectively. The measurement signals associated with each of these pixels are used for model training and measurement. FIG. 21 depicts a vector 436 of measured intensity (e.g., reflectance) values sampled at the pixel locations illustrated in FIG. 20. This sampled image data is used for model training and measurement. In the example depicted in FIG. 21, $^1I_{(I1,J1)}$ is the intensity value associated with pixel 430 of image 422, $^2I_{(I1,J1)}$ is the intensity value associated with pixel 432 of image 423, and $^NI_{(I1,J1)}$ is the intensity value associated with pixel 434 of image 424. Similarly, $^1I_{(I2,J2)}$ is the intensity value associated with pixel 431 of image 422, $^2I_{(I2,J2)}$ is the intensity value associated with pixel 432 of image 423, and $^NI_{(I2,J2)}$ is the intensity value associated with pixel 435 of image 424. In this manner, vector 436 includes intensity measurement signals from pixels at the same location of each imaged measurement site.

In some examples, pixel locations are selected randomly. In some other examples, the pixel locations are selected based on their measurement sensitivity. In one example, the variance of measurement signal values associated with each pixel location is calculated from the ensemble of images.

The variance associated with each pixel location is a metric that characterizes the measurement sensitivity at each corresponding pixel location. Pixel locations with relatively high variance offer higher measurement sensitivity and are selected for further analysis. Pixel locations with relatively low variance offer lower measurement sensitivity and are discarded. In some examples, a predetermined threshold value for variance is selected, and pixel locations with a variance that exceeds the predetermined threshold value are selected for model training and measurement. In this manner, only the most sensitive locations are sampled. In some examples, all of the pixels associated with each of the first plurality of images are selected for model training and measurement. In this sense, block 404 is optional.

In block 405, a feature extraction model is determined based on the selected image data. The feature extraction model reduces a dimension of the image data. A feature extraction model maps the original signals to a new reduced set of signals. The transformation is determined based on the variations in the parameter(s) of interest in the selected images. Each pixel of each image is treated as an original signal that changes within the process range for different images. The feature extraction model may be applied to all of the image pixels, or a subset of image pixels. In some examples, the pixels subject to analysis by the feature extraction model are chosen randomly. In some other examples, the pixels subject to analysis by the feature extraction model are chosen due to their relatively high sensitivity to changes in the parameter(s) of interest. For example, pixels that are not sensitive to changes in the parameter(s) of interest may be ignored.

By way of non-limiting example, the feature extraction model may a principal component analysis (PCA) model, a kernel PCA model, a non-linear PCA model, an independent component analysis (ICA) model or other dimensionality reduction methods using dictionaries, a discrete cosine transform (DCT) model, fast fourier transform (FFT) model, a wavelet model, etc.

Figure 22:
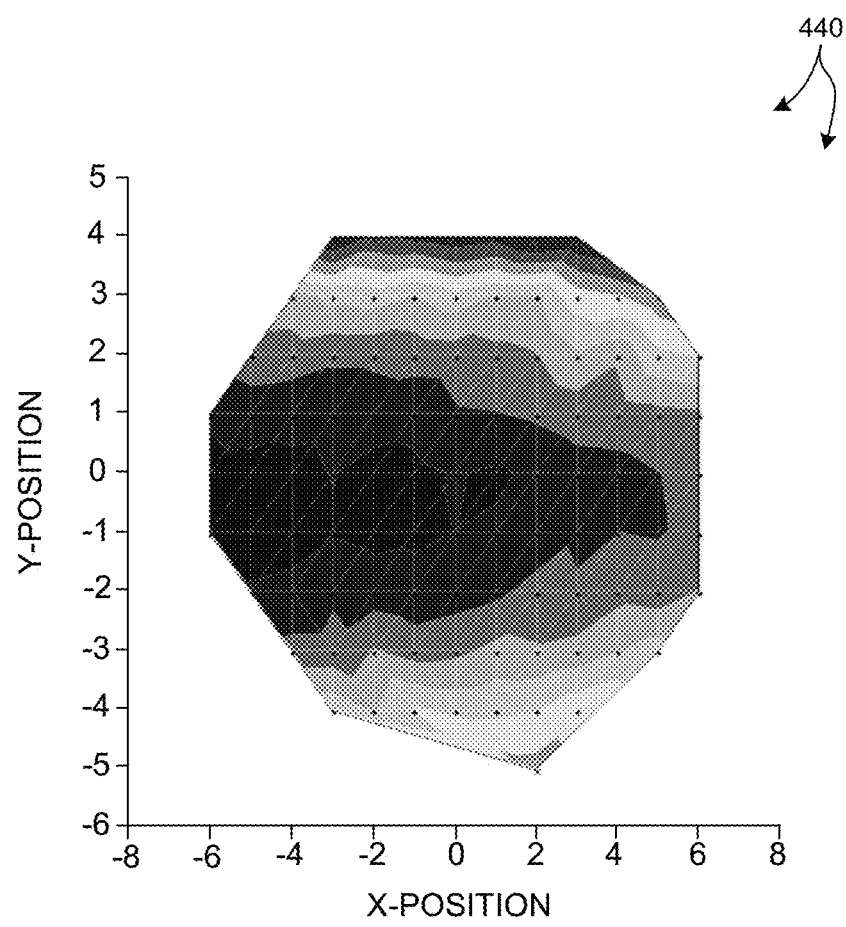
FIG. 22 illustrates a contour plot 440 of values of a single principal component of the images of wafer 420.

FIG. 22 illustrates a contour plot 440 of values of a single principal component of the images of wafer 420. As illustrated, this principal component indicates the presence of systematic behavior across the image data set (i.e., change of focus). In this example, it is preferred to utilize this principal component to train an image based measurement model that is sensitive to focus. In general, principal components that primarily reflect noise are truncated for purposes of model building, and subsequent image-based measurement analysis.

In a typical design of experiments, the locations on the wafer are programmed to have specific geometric and process parameter values (e.g., focus, dose, overlay, CD, SWA, Ht etc.). Hence the principal components representation allows mapping one or more signal representations as a function of process parameters over the entire wafer. The nature of the pattern captures the essential properties of the device, whether it included isolated or dense features.

In block 406, an image based measurement model is trained based on features extracted from the plurality of images and the known values of the at least one parameter of interest. The image-based measurement model is structured to receive image data generated by a metrology system at one or more measurement sites, and directly determine the parameter(s) of interest associated with each measurement target. In some embodiments, the image-based measurement model is implemented as a neural network model. In one example, the number of nodes of the neural network is selected based on the features extracted from the image data.

In other examples, the image-based measurement model may be implemented as a linear model, a polynomial model, a response surface model, a support vector machines model, or other types of models. In some examples, the image-based measurement model may be implemented as a combination of models. The selected model is trained based on the reduced set of signals determined from the feature extraction model and the known variations in the parameter(s) of interest. The model is trained such that its output fits the defined variations in the parameter(s) of interest for all the images in the parameter variation space defined by the DOE images.

Figure 16:
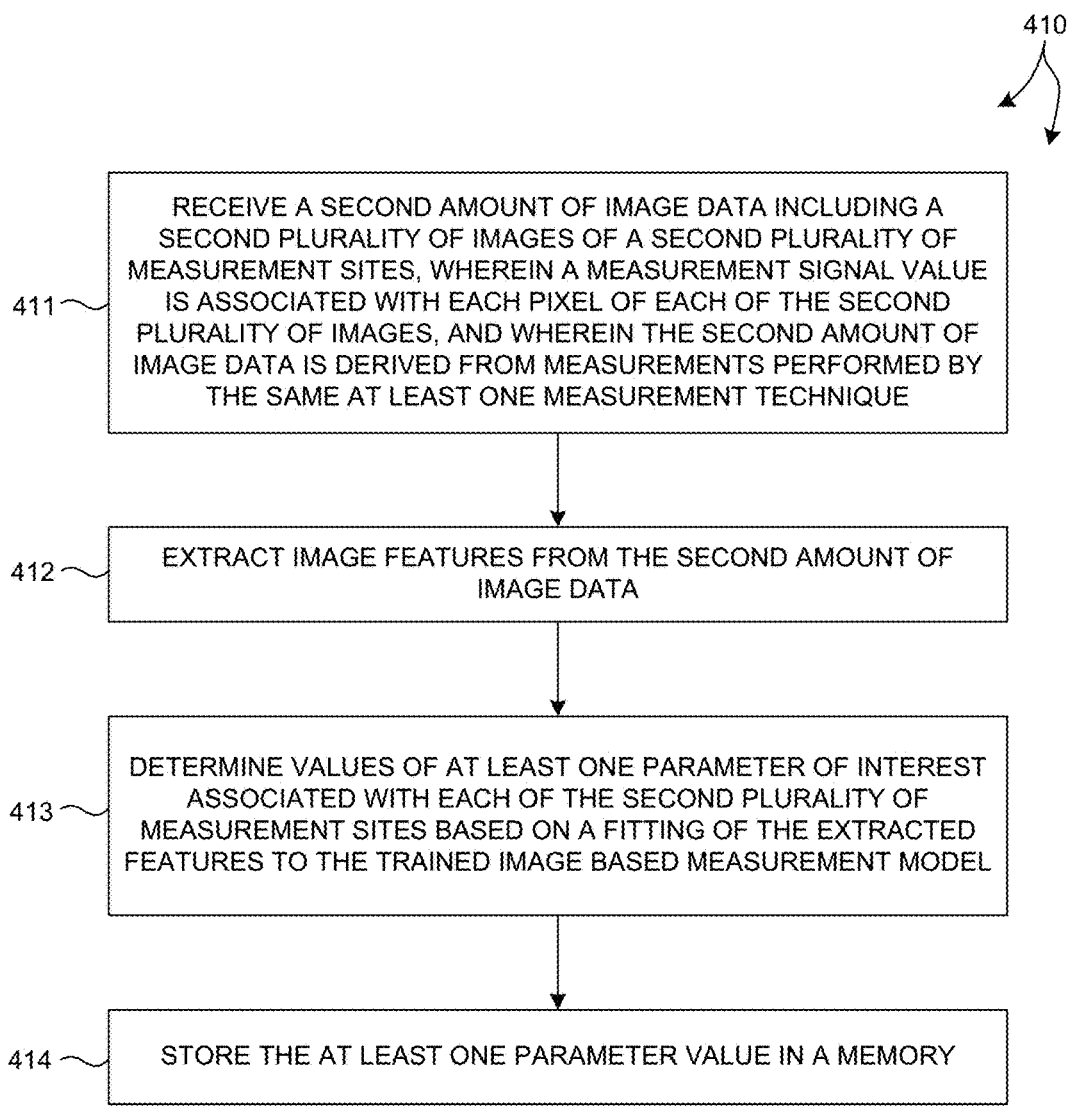
FIG. 16 is a flowchart illustrative of a method 410 of performing measurements of a structure using a trained measurement model as described with reference to method 400.

In another aspect, the trained model is employed as the measurement model for measurement of other wafers. FIG. 16 illustrates a method 410 suitable for implementation by a metrology system such as metrology system 500 illustrated in FIG. 31 of the present invention. In one aspect, it is recognized that data processing blocks of method 410 may be carried out via a pre-programmed algorithm executed by one or more processors of computing system 530, or any other general purpose computing system. It is recognized herein that the particular structural aspects of metrology system 500 do not represent limitations and should be interpreted as illustrative only.

In block 411, an amount of image data associated with images of a plurality of sites on a surface of a semiconductor wafer is received by a computing system (e.g., computing system 530). The image data is derived from measurements performed by the same metrology technique, or combination of metrology techniques as described with reference to method 400. A measurement signal value is associated with each pixel of each of the received images. The image data includes images of the same types of structures as described with reference to method 400, but with unknown values of one or more parameters of interest.

The image data is subjected to the same alignment, filtering, and sampling steps described with reference to blocks 402, 403, and 404 of method 400. Although, the use of any, or all, of these steps may be advantageous, in general, it is not necessary. In this sense, these steps are optional.

In block 412, image features are extracted from at least a portion of the amount of image data. It is preferred to extract features from the image data by applying the same feature extraction model used for model training. (e.g., the feature extraction model described with reference to step 405 of method 400). In this manner, the dimension reduction of the acquired image data is performed by the same feature extraction model used to reduce the dimension of the training data.

In block 413, the value of at least one parameter of interest associated with each of the plurality of measurement sites is determined based on a fitting of the extracted image features to a trained image-based measurement model (e.g., the trained image-based measurement model described with reference to method 400). In this manner, the parameter(s) of interest are determined based on the trained image-based measurement model and the reduced set of image signals.

In block 414, the determined value(s) of the parameter(s) of interest are stored in a memory. For example, the parameter values may be stored on-board the measurement system 500, for example, in memory 532, or may be communicated (e.g., via output signal 540) to an external memory device.

In some examples, the measurement performance of the trained image-based measurement model is determined by using the model to measure a set of images that have not participated as part of the training data set, but have known values of the parameter(s) of interest. The differences between the expected and measured overlay are indicative of model performance.

Figure 23:
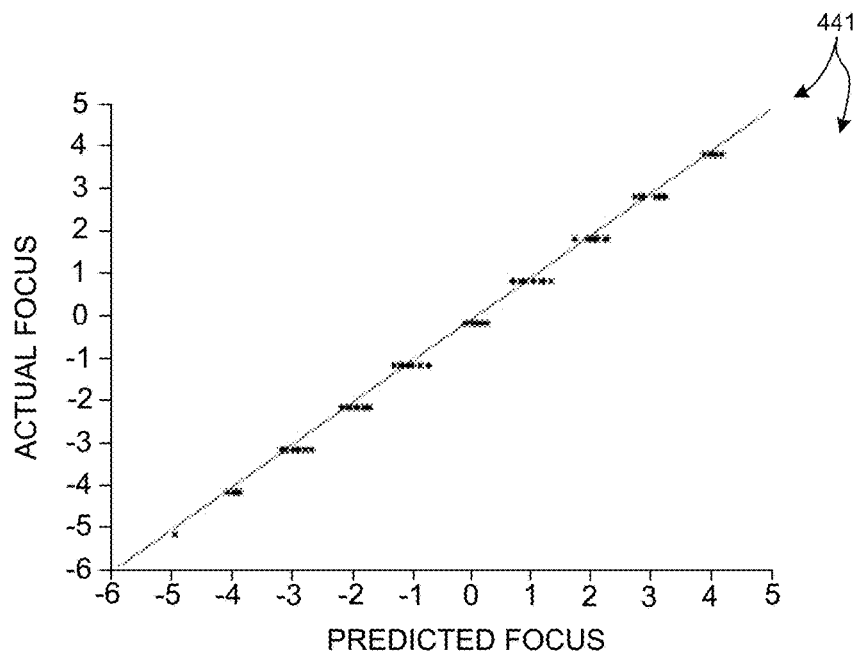
FIG. 23 depicts a plot 441 of simulation results indicative of actual focus error on the y-axis and corresponding predicted focus error on the x-axis.

FIG. 23 depicts a plot 441 of simulation results indicative of actual focus error on the y-axis (i.e., known focus error values) and corresponding predicted focus error on the x-axis (i.e., as measured by a trained image-based measurement model). The results depicted in plot 441 include measurements of images that participated in the training set and images that did not participate in the training set. As depicted in FIG. 23, the simulated measurement results are tightly grouped with the corresponding, known values.

Figure 24:
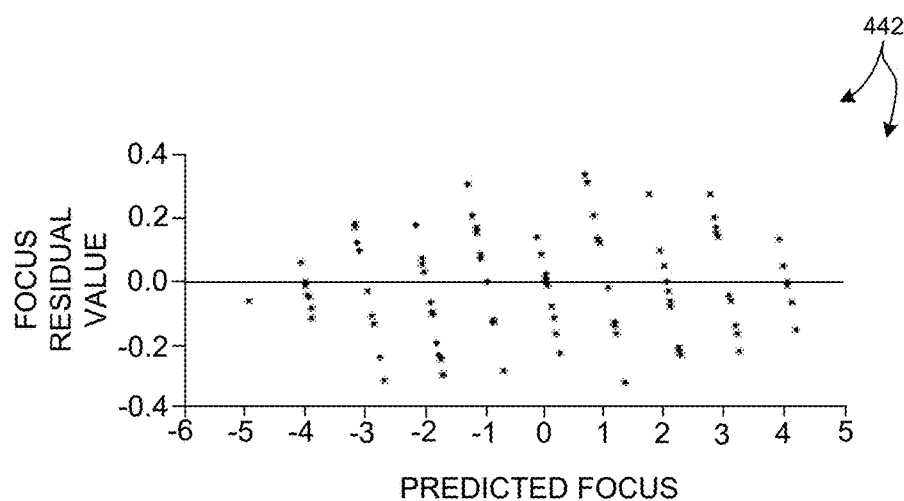
FIG. 24 depicts a plot 442 indicative of the residual focus error values associated with each measurement point depicted in FIG. 23.

FIG. 24 depicts a plot 442 indicative of the residual focus error values associated with each measurement point depicted in FIG. 23. The residual focus error value is the difference between the actual focus error value and the predicted focus error value.

As described hereinbefore, the measurement methods and systems described herein are not constrained to specialized targets. In general, any target that exhibits sensitivity to a parameter of interest when imaged by the available imaging system may be employed in accordance with the methods and systems described herein.

However, in some examples, it is advantageous to employ specialized measurement targets that exhibit high sensitivity to a parameter of interest when imaged by the available imaging system to enhance image-based measurement performance. For example, when signal response metrology is applied to the measurement of overlay error as described herein, it is desirable to maximize the number of pixels that change due to changes in overlay error in the x and y directions.

FIGS. 25A-25B exhibit a nine cell metrology target that may be advantageous for image-based measurement of parameters of interest.

Figure 26:
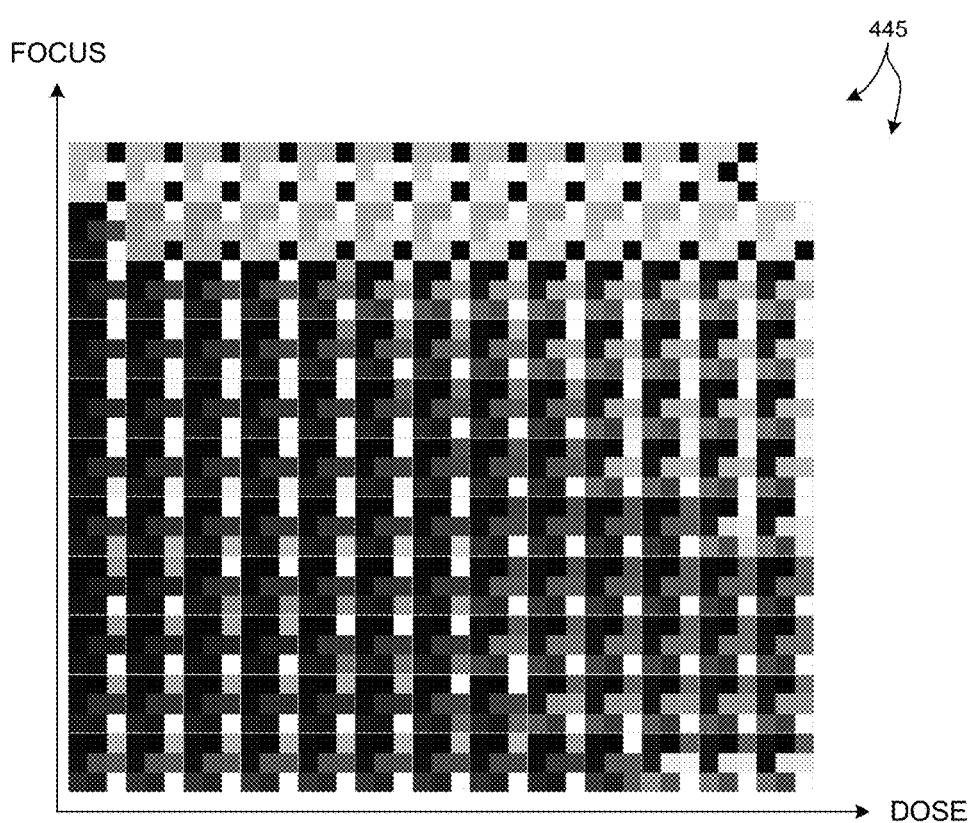
FIG. 26 depicts a simulated image 445 of a number of measurement sites each including an instance of the nine cell metrology target depicted in FIGS. 25A-B.

FIG. 26 depicts a simulated image 445 of a number of measurement sites each including one instance of the nine cell metrology target depicted in FIGS. 25A-B. Each nine cell target is subjected to different focus and dose conditions depending on its location in image 445. Thus, each nine cell image within simulated image 445 corresponds to an image of the nine cell target under a specific combination of focus and dose. As illustrated in FIG. 26, the intensity corresponding to each specific device structure evolves differently as a function of focus and dose.

Following the steps of method 400, these images were processed to train a linear image based measurement model. Since the simulated measurement sites are small, all pixels were sampled to construct the intensity vector. This resulted in a 9 element (3×3) vector of measurement signals, collected for a range of 13 dose and 11 focus values.

The simulated image 445 is measured with a wavelength of 637 nanometers. However, in addition, the same ensemble of measurement sites was measured with illumination light at 523 nanometers and 467 nanometers.

Figure 27A:
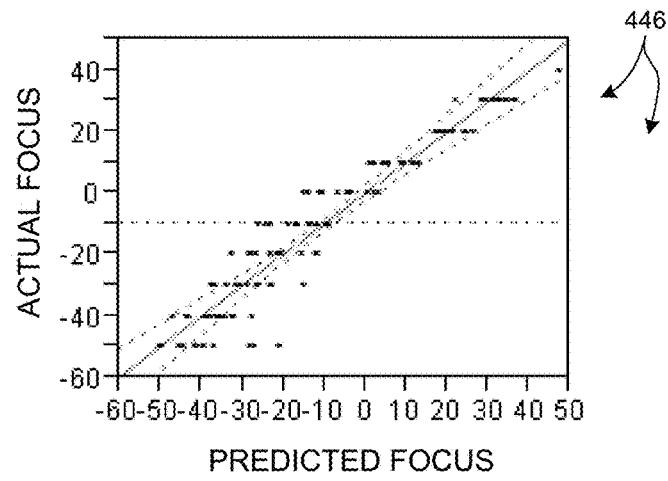
FIGS. 27A-C depict plots 446-448, respectively, illustrating simulation results indicative of actual focus error on the y-axis and corresponding predicted focus error on the x-axis for measurement data associated with measurements at 637 nanometers, 523 nanometers, and 467 nanometers, respectively.

FIG. 27A depicts plot 446 of simulation results indicative of actual focus error on the y-axis (i.e., known focus error values) and corresponding predicted focus error on the x-axis (i.e., as measured by a trained image-based measurement model). The results depicted in plot 446 include measurements of images that participated in the training set and images that did not participate in the training set. In this example, measurement data associated with measurements at 637 nanometers were used for model training and measurement.

Figure 27B:
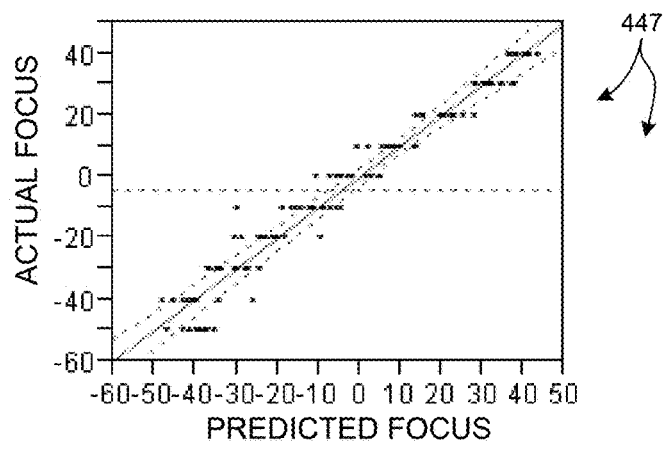

FIG. 27B depicts plot 447 of simulation results indicative of actual focus error on the y-axis (i.e., known focus error values) and corresponding predicted focus error on the x-axis (i.e., as measured by a trained image-based measurement model). The results depicted in plot 447 include measurements of images that participated in the training set and images that did not participate in the training set. In this example, measurement data associated with measurements at 523 nanometers were used for model training and measurement.

Figure 27C:
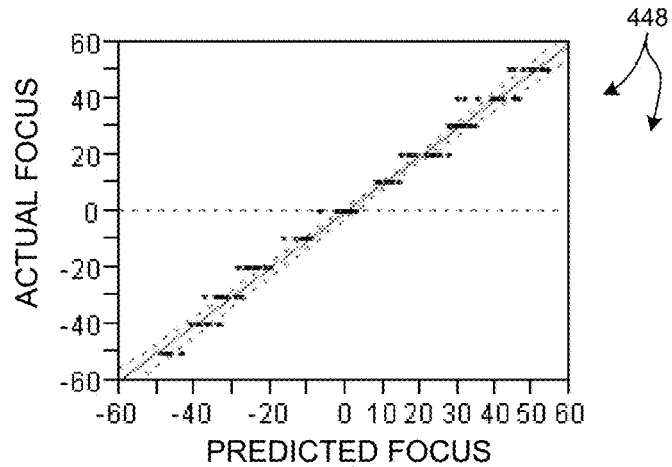

FIG. 27C depicts plot 448 of simulation results indicative of actual focus error on the y-axis (i.e., known focus error values) and corresponding predicted focus error on the x-axis (i.e., as measured by a trained image-based measurement model). The results depicted in plot 448 include measurements of images that participated in the training set and images that did not participate in the training set. In this example, measurement data associated with measurements at 467 nanometers were used for model training and measurement.

Figure 28A:
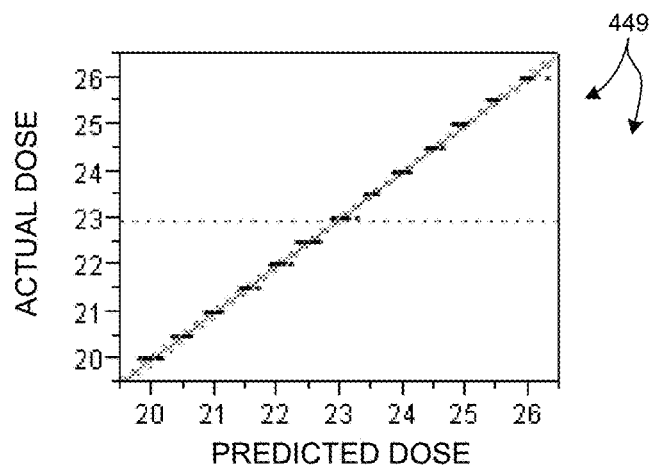
FIGS. 28A-C depict plots 449-451, respectively, illustrating simulation results indicative of actual dosage error on the y-axis and corresponding predicted dosage error on the x-axis for measurement data associated with measurements at 637 nanometers, 523 nanometers, and 467 nanometers, respectively.

FIG. 28A depicts plot 449 of simulation results indicative of actual dosage error on the y-axis (i.e., known dosage error values) and corresponding predicted dosage error on the x-axis (i.e., as measured by a trained image-based measurement model). The results depicted in plot 449 include measurements of images that participated in the training set and images that did not participate in the training set. In this example, measurement data associated with measurements at 637 nanometers were used for model training and measurement.

Figure 28B:
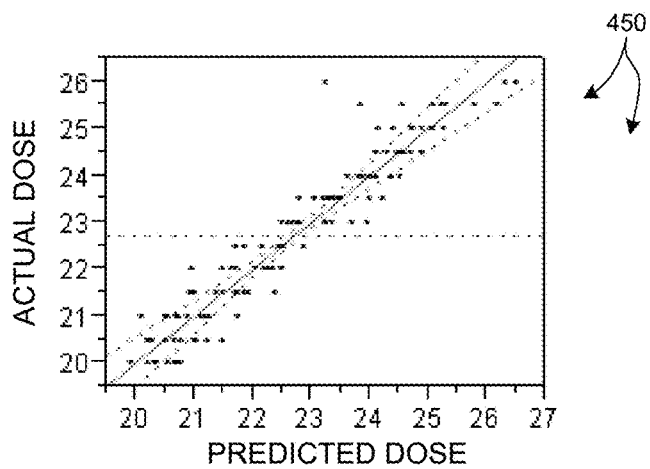

FIG. 28B depicts plot 450 of simulation results indicative of actual dosage error on the y-axis (i.e., known dosage error values) and corresponding predicted dosage error on the x-axis (i.e., as measured by a trained image-based measurement model). The results depicted in plot 450 include measurements of images that participated in the training set and images that did not participate in the training set. In this example, measurement data associated with measurements at 523 nanometers were used for model training and measurement.

Figure 28C:
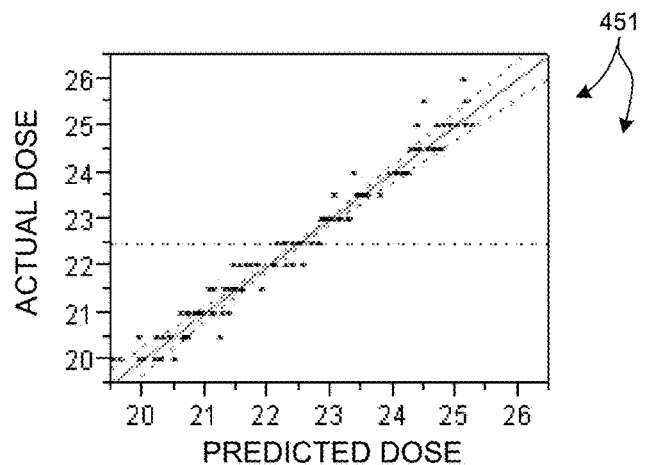

FIG. 28C depicts plot 451 of simulation results indicative of actual dosage error on the y-axis (i.e., known dosage error values) and corresponding predicted dosage error on the x-axis (i.e., as measured by a trained image-based measurement model). The results depicted in plot 451 include measurements of images that participated in the training set and images that did not participate in the training set. In this example, measurement data associated with measurements at 467 nanometers were used for model training and measurement.

For each wavelength selected for the analysis, the R-squared value of the agreement between the actual and the predicted value is above the statistically acceptable limit of 0.75. It should be recognized that each image included only nine measurement values for these experiments, hence these results have been generated at a statistical power lower than what is usually achieved in ideal cases.

Figure 29:
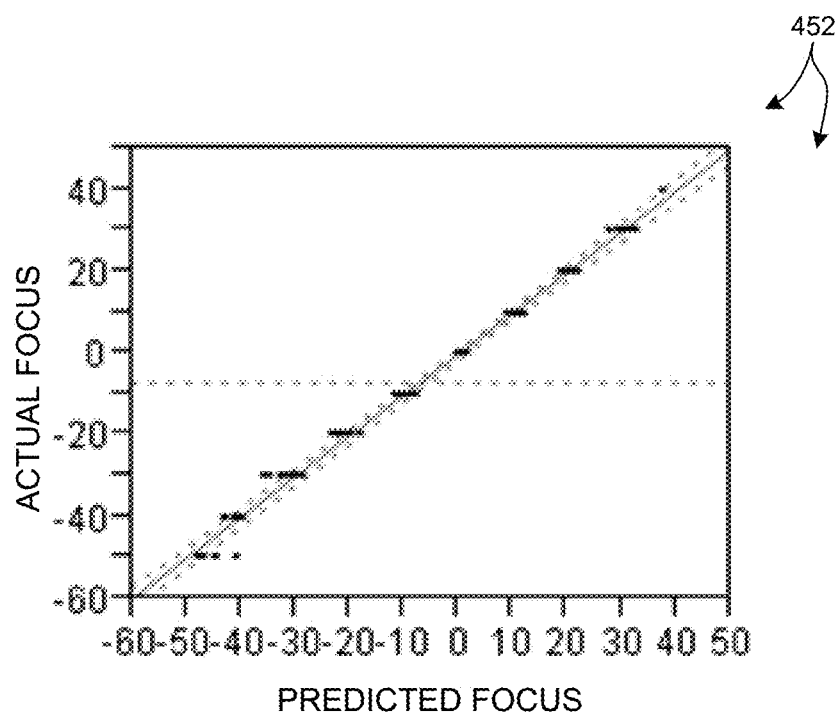
FIG. 29 depicts plot 452 of simulation results indicative of actual focus error on the y-axis and corresponding predicted focus error on the x-axis for combined measurement data associated with measurements at 467, 523, and 467 nanometers.
Figure 30:
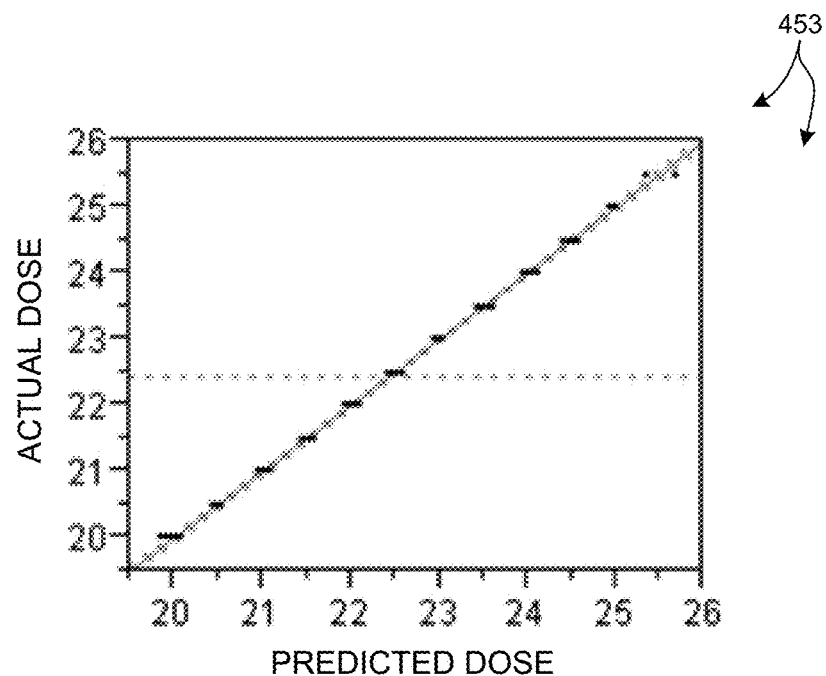
FIG. 30 depicts plot 453 of simulation results indicative of actual dosage error on the y-axis and corresponding predicted dosage error on the x-axis for combined measurement data associated with measurements at 467, 523, and 467 nanometers.

In another example, measurement results at multiple wavelengths are combined for model training and measurement. FIG. 29 depicts plot 452 of simulation results indicative of actual focus error on the y-axis (i.e., known focus error values) and corresponding predicted focus error on the x-axis (i.e., as measured by a trained image-based measurement model). The results depicted in plot 452 include measurements of images that participated in the training set and images that did not participate in the training set. In this example, measurement data associated with measurements at 467, 523, and 467 nanometers were used for model training and measurement. FIG. 30 depicts plot 453 of simulation results indicative of actual dosage error on the y-axis (i.e., known dosage error values) and corresponding predicted dosage error on the x-axis (i.e., as measured by a trained image-based measurement model). The results depicted in plot 453 include measurements of images that participated in the training set and images that did not participate in the training set. In this example, measurement data associated with measurements at 467, 523, and 467 nanometers were used for model training and measurement.

Comparing the results depicted in FIGS. 27A-C and 28A-C with the results of FIGS. 29 and 30, it is clear that combining multiple wavelengths results in predicted values that are closer to the actual values of the parameters of interest.

In another further aspect, the methods and systems for training the image-based measurement model include an optimization algorithm to automate any or all of the elements required to arrive at a trained image-based measurement model.

In some examples, an optimization algorithm is configured to maximize the performance of the measurement (defined by a cost function) by optimizing any or all of the following parameters: the list of image filters, the parameters of the filters, pixel sampling, the type of feature extraction model, the parameters of the selected feature extraction model, the type of measurement model, the parameters of the selected measurement model. The optimization algorithm can include user defined heuristics and can be combination of nested optimizations (e.g., combinatorial and continuous optimization).

In a further aspect, image data from different targets is collected for model building, training, and measurement. The use of image data associated with multiple targets having different structure, but formed by the same process conditions increases the information embedded in the model and reduces the correlation to process or other parameter variations. In particular, the use of training data that includes images of multiple, different targets at one or more measurement sites enables more accurate estimation of values of parameters of interest.

In another further aspect, signals from multiple targets can be processed to reduce sensitivity to process variations and increase sensitivity to the parameters of interest. In some examples, signals from images, or portions of images, of different targets are subtracted from one another. In some other examples, signals from images, or portions of images, of different targets are fit to a model, and the residuals are used to build, train, and use the image-based measurement model as described herein. In one example, image signals from two different targets are subtracted to eliminate, or significantly reduce, the effect of process noise in each measurement result. In general, various mathematical operations can be applied between the signals from different target images, or portions of target images to determine image signals with reduced sensitivity to process variations and increased sensitivity to the parameters of interest.

In another further aspect, measurement data derived from measurements performed by a combination of multiple, different measurement techniques is collected for model building, training, and measurement. The use of measurement data associated with multiple, different measurement techniques increases the information content in the combined set of signals and reduces the correlation to process or other parameters variations. Different measurement sites may be measured by multiple, different measurement techniques (e.g., CD-SEM, imaging techniques such as 2-D BPR, scatterometry, etc.) to enhance the measurement information available for estimation of parameters of interest.

In general, any image based measurement technique, or combination of two or more measurement techniques may be contemplated within the scope of this patent document as the data processed by the feature extraction model and the image-based measurement model for training and measurement is in vector form. Because the signal response metrology techniques as described herein operate on vectors of data, each pixel of image data is treated independently. In addition, it is possible to concatenate data from multiple, different metrologies, regardless of whether the data is two dimensional image data, one dimensional image data, or even single point data.

Exemplary measurement techniques that may provide data for analysis in accordance with the signal response metrology techniques described herein include, but are not limited to spectroscopic ellipsometry, including Mueller matrix ellipsometry, spectroscopic reflectometry, spectroscopic scatterometry, scatterometry overlay, beam profile reflectometry, both angle-resolved and polarization-resolved, beam profile ellipsometry, single or multiple discrete wavelength ellipsometry, transmission small angle x-ray scatterometer (TSAXS), small angle x-ray scattering (SAXS), grazing incidence small angle x-ray scattering (GISAXS), wide angle x-ray scattering (WAXS), x-ray reflectivity (XRR), x-ray diffraction (XRD), grazing incidence x-ray diffraction (GIXRD), high resolution x-ray diffraction (HRXRD), x-ray photoelectron spectroscopy (XPS), x-ray fluorescence (XRF), grazing incidence x-ray fluorescence (GIXRF), x-ray tomography, and x-ray ellipsometry. In general, any image based metrology technique applicable to the characterization of semiconductor structures may be contemplated, individually, or in any combination.

In another further aspect, signals measured by multiple metrologies can be processed to reduce sensitivity to process variations and increase sensitivity to the parameters of interest. In some examples, signals from images, or portions of images, of targets measured by different metrologies are subtracted from one another. In some other examples, signals from images, or portions of images, of targets measured by different metrologies are fit to a model, and the residuals are used to build, train, and use the image-based measurement model as described herein. In one example, image signals from a target measured by two different metrologies are subtracted to eliminate, or significantly reduce, the effect of process noise in each measurement result. In general, various mathematical operations can be applied between the signals of target images, or portions of target images, measured by different metrologies to determine image signals with reduced sensitivity to process variations and increased sensitivity to the parameters of interest.

In general, image signals from multiple targets each measured by multiple metrology techniques increases the information content in the combined set of signals and reduces the overlay correlation to process or other parameters variations.

FIG. 31 illustrates a system 500 for measuring characteristics of a specimen in accordance with methods 400 and 410 presented herein. As shown in FIG. 31, the system 500 may be used to perform spectroscopic ellipsometry measurements of one or more structures of a specimen 501. In this aspect, the system 500 may include a spectroscopic ellipsometer equipped with an illuminator 502 and a spectrometer 504. The illuminator 502 of the system 500 is configured to generate and direct illumination of a selected wavelength range (e.g., 150-850 nm) to the structure disposed on the surface of the specimen 501. In turn, the spectrometer 504 is configured to receive illumination reflected from the surface of the specimen 501. It is further noted that the light emerging from the illuminator 502 is polarized using a polarization state generator 507 to produce a polarized illumination beam 506. The radiation reflected by the structure disposed on the specimen 501 is passed through a polarization state analyzer 509 and to the spectrometer 504. The radiation received by the spectrometer 504 in the collection beam 508 is analyzed with regard to polarization state, allowing for spectral analysis by the spectrometer of radiation passed by the analyzer. These spectra 511 are passed to the computing system 530 for analysis of the structure.

As depicted in FIG. 31, system 500 includes a single measurement technology (i.e., SE). However, in general, system 500 may include any number of different measurement technologies. By way of non-limiting example, system 500 may be configured as a spectroscopic ellipsometer (including Mueller matrix ellipsometry), a spectroscopic reflectometer, a spectroscopic scatterometer, an overlay scatterometer, an angular resolved beam profile reflectometer, a polarization resolved beam profile reflectometer, a beam profile reflectometer, a beam profile ellipsometer, any single or multiple wavelength ellipsometer, or any combination thereof. Furthermore, in general, measurement data collected by different measurement technologies and analyzed in accordance with the methods described herein may be collected from multiple tools, rather than one tool integrating multiple technologies.

In a further embodiment, system 500 may include one or more computing systems 530 employed to perform measurements based on image-based measurement models developed in accordance with the methods described herein. The one or more computing systems 530 may be communicatively coupled to the spectrometer 504. In one aspect, the one or more computing systems 530 are configured to receive measurement data 511 associated with measurements of the structure of specimen 501.

It should be recognized that the various steps described throughout the present disclosure may be carried out by a single computer system 530 or, alternatively, a multiple computer system 530. Moreover, different subsystems of the system 500, such as the spectroscopic ellipsometer 504, may include a computer system suitable for carrying out at least a portion of the steps described herein. Therefore, the aforementioned description should not be interpreted as a limitation on the present invention but merely an illustration. Further, the one or more computing systems 530 may be configured to perform any other step(s) of any of the method embodiments described herein.

In addition, the computer system 530 may be communicatively coupled to the spectrometer 504 in any manner known in the art. For example, the one or more computing systems 530 may be coupled to computing systems associated with the spectrometer 504. In another example, the spectrometer 504 may be controlled directly by a single computer system coupled to computer system 530.

The computer system 530 of the metrology system 500 may be configured to receive and/or acquire data or information from the subsystems of the system (e.g., spectrometer 504 and the like) by a transmission medium that may include wireline and/or wireless portions. In this manner, the transmission medium may serve as a data link between the computer system 530 and other subsystems of the system 500.

Computer system 530 of metrology system 500 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 530 and other systems (e.g., memory on-board metrology system 500, external memory, or other external systems). For example, the computing system 530 may be configured to receive measurement data from a storage medium (i.e., memory 532 or an external memory) via a data link. For instance, spectral results obtained using spectrometer 504 may be stored in a permanent or semi-permanent memory device (e.g., memory 532 or an external memory). In this regard, the spectral results may be imported from on-board memory or from an external memory system. Moreover, the computer system 530 may send data to other systems via a transmission medium. For instance, a trained measurement model or a specimen parameter 540 determined by computer system 530 may be communicated and stored in an external memory. In this regard, measurement results may be exported to another system.

Computing system 530 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 534 implementing methods such as those described herein may be transmitted over a transmission medium such as a wire, cable, or wireless transmission link. For example, as illustrated in FIG. 31, program instructions 534 stored in memory 532 are transmitted to processor 531 over bus 533. Program instructions 534 are stored in a computer readable medium (e.g., memory 532). Exemplary computer-readable media include read-only memory, a random access memory, a magnetic or optical disk, or a magnetic tape.

In yet another aspect, the measurement results described herein can be used to provide active feedback to a process tool (e.g., lithography tool, etch tool, deposition tool, etc.). For example, values of overlay error determined using the methods described herein can be communicated to a lithography tool to adjust the lithography system to achieve a desired output. In a similar way etch parameters (e.g., etch time, diffusivity, etc.) or deposition parameters (e.g., time, concentration, etc.) may be included in a measurement model to provide active feedback to etch tools or deposition tools, respectively.

In general, the systems and methods described herein can be implemented as part of the process of preparing a measurement model for off-line or on-tool measurement. In addition, the measurement model may describe one or more target structures, device structures, and measurement sites.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method comprising:
providing a first overlay target having a first grating structure located in a first layer and a second grating structure located in a subsequent layer, wherein the second grating structure is offset from the first grating structure by a known offset distance in a first direction;
providing a second overlay target having a first grating structure located in the first layer and a second grating structure located in the subsequent layer, wherein the second grating structure is offset by the known offset distance in a second direction, opposite the first direction;
receiving a first amount of scatterometry data associated with a measurement of the first overlay target at a first azimuth angle and a second amount of scatterometry data associated with a measurement of the first overlay target from a second azimuth angle;
determining a first differential measurement signal for the first overlay target based on a difference between the first amount of scatterometry data and the second amount of scatterometry data;
receiving a third amount of scatterometry data associated with a measurement of the second overlay target at the first azimuth angle and a fourth amount of scatterometry data associated with a measurement of the second overlay target from the second azimuth angle;
determining a second differential measurement signal for the second overlay target based on a difference between the third amount of scatterometry data and the fourth amount of scatterometry data; and
determining an overlay error between the first grating structures of the first and second overlay targets and the second grating structures of the first and second overlay targets based at least in part on the first and second differential measurement signals.

2. The method of claim 1, wherein the first, second, third, and fourth amounts of scatterometry data include measurements at multiple illumination wavelengths.

3. The method of claim 2, wherein the determining of the first differential measurement signal involves a summation of a plurality of differential measurement signals each determined for the first overlay target based on a difference between the first amount of scatterometry data and the second amount of scatterometry data at each of the multiple illumination wavelengths, and wherein the determining of the second differential measurement signal involves a summation of a plurality of differential measurement signals each determined for the second overlay target based on a difference between the third amount of scatterometry data and the fourth amount of scatterometry data at each of the multiple illumination wavelengths.

4. The method of claim 2, wherein the determining of the first differential measurement signal involves a weighted summation of a plurality of differential measurement signals each determined for the first overlay target based on a difference between the first amount of scatterometry data and the second amount of scatterometry data at each of the multiple illumination wavelengths, and wherein the determining of the second differential measurement signal involves a weighted summation of a plurality of differential measurement signals each determined for the second overlay target based on a difference between the third amount of scatterometry data and the fourth amount of scatterometry data at each of the multiple illumination wavelengths.

5. The method of claim 4, further comprising:
providing a plurality of overlay training targets each having a first grating structure located in a first layer and a second grating structure located in a subseqent layer, wherein each of the first grating structures and each of the second grating structure are offset by different, known overlay values;
receiving a fifth amount of scatterometry data associated with measurements of each of the overlay training targets at the first azimuth angle and a sixth amount of scatterometry data associated with measurements of each of the overlay training targets from the second azimuth angle;
determining a plurality of differential measurement signals, each differential measurement signal of the plurality based on a difference between a portion of the fifth amount of scatterometry data and a portion of the sixth amount of scatterometry data associated with each of the overlay training targets; and
determining a plurality of weighting values of the weighted summation based on a fitting of a linear combination of principal components of each of the plurality of differential measurement signals to a function of the known overlay values.

6. The method of claim 1, further comprising:
providing a metrology target having a process induced asymmetry;
receiving a fifth amount of scatterometry data associated with a measurement of the metrology target at the first azimuth angle and a sixth amount of scatterometry data associated with a measurement of the metrology target at the second azimuth angle;
transforming the fifth and sixth amounts of scatterometry data from coordinates in a measurement domain to coordinates of the metrology target in an alternate domain;
transforming the first and second amounts of scatterometry data from coordinates in a measurement domain to coordinates of the first overlay target in the alternate domain;
fitting a linear model of the principal components of the metrology target to the principal components of the first overlay target;
determining residuals of the fit of the linear model of the principal components of the metrology target to the principal components of the first overlay target, wherein the determining of the first differential measurement signal for the first overlay target is based on a difference between the residuals associated with the first amount of scatterometry data and the residuals associated with the second amount of scatterometry data.

7. The method of claim 6, wherein the metrology target includes a grating structure located in the first layer, the grating structure of the metrology target and the first grating structure of the first overlay target having a process induced asymmetry.

8. The method of claim 6, wherein the metrology target includes a grating structure located in the subsequent layer, the grating structure of the metrology target and the second grating structure of the first overlay target having a process induced asymmetry.

9. The method of claim 6, wherein the transforming involves any of a principal component analysis (PCA), an independent component analysis (ICA), a kernel PCA, a non-linear PCA, a fast Fourier transform (FFT) analysis, a discrete cosine transform (DCT) analysis, and a wavelet analysis.

10. An overlay metrology system comprising:
an illumination source configured to supply an amount of illumination light to a specimen;
a detector configured to collect an amount of zero order diffracted light from a first overlay target and a second overlay target at a first azimuth angle and a second azimuth angle,
the first overlay target having a first grating structure located in a first layer of the specimen and a second grating structure located in a subsequent layer of the specimen, wherein the second grating structure is offset from the first grating structure by a known offset distance in a first direction, and
the second overlay target having a first grating structure located in the first layer and a second grating structure located in the subsequent layer, wherein the second grating structure is offset by a known offset distance in a second direction, opposite the first direction; and
a computing system configured to:
receive a first amount of scatterometry data associated with a measurement of the first overlay target at the first azimuth angle and a second amount of scatterometry data associated with a measurement of the first overlay target from the second azimuth angle;
determine a first differential measurement signal for the first overlay target based on a difference between the first amount of scatterometry data and the second amount of scatterometry data;
receive a third amount of scatterometry data associated with a measurement of the second overlay target at the first azimuth angle and a fourth amount of scatterometry data associated with a measurement of the second overlay target from the second azimuth angle;
determine a second differential measurement signal for the second overlay target based on a difference between the third amount of scatterometry data and the fourth amount of scatterometry data; and determine an overlay error between the first grating structures of the first and second overlay targets and the second grating structures of the first and second overlay targets based at least in part on the first and second differential measurement signals.

11. The overlay metrology system of claim 10, wherein the first, second, third, and fourth amounts of scatterometry data include measurements at multiple illumination wavelengths.

12. The overlay metrology system of claim 11, wherein the determining of the first differential measurement signal involves a summation of a plurality of differential measurement signals each determined for the first overlay target based on a difference between the first amount of scatterometry data and the second amount of scatterometry data at each of the multiple illumination wavelengths, and wherein the determining of the second differential measurement signal involves a summation of a plurality of differential measurement signals each determined for the second overlay target based on a difference between the third amount of scatterometry data and the fourth amount of scatterometry data at each of the multiple illumination wavelengths.

13. The overlay metrology system of claim 11, wherein the determining of the first differential measurement signal involves a weighted summation of a plurality of differential measurement signals each determined for the first overlay target based on a difference between the first amount of scatterometry data and the second amount of scatterometry data at each of the multiple illumination wavelengths, and wherein the determining of the second differential measurement signal involves a weighted summation of a plurality of differential measurement signals each determined for the second overlay target based on a difference between the third amount of scatterometry data and the fourth amount of scatterometry data at each of the multiple illumination wavelengths.

14. The overlay metrology system of claim 13, wherein the detector is further configured to collect an amount of zero order diffracted light at the first azimuth angle and the second azimuth angle from a plurality of overlay training targets each having a first grating structure located in a first layer and a second grating structure located in a subsequent layer, wherein each of the first grating structures and each of the second grating structures are offset by different, known overlay values, and wherein the computing system is further configured to:

receive a fifth amount of scatterometry data associated with measurements of each of the overlay training targets at the first azimuth angle and a sixth amount of scatterometry data associated with measurements of each of the overlay training targets at the second azimuth angle;

determine a plurality of differential measurement signals, each differential measurement signal of the plurality based on a difference between a portion of the fifth amount of scatterometry data and a portion of the sixth amount of scatterometry data associated with each of the overlay training targets; and determine a plurality of weighting values of the weighted summation based on a fitting of a linear combination of principal components of each of the plurality of differential measurement signals to a function of the known overlay values.

15. The overlay metrology system of claim 10, wherein detector is further configured to collect an amount of zero order diffracted light at the first azimuth angle and the second azimuth angle from a metrology target having a process induced asymmetry, and wherein the computing system is further configured to:

receive a fifth amount of scatterometry data associated with a measurement of the metrology target at the first azimuth angle and a sixth amount of scatterometry data associated with a measurement of the metrology target at the second azimuth angle;

transform the fifth and sixth amounts of scatterometry data from coordinates in a measurement domain to coordinates of the metrology target in an alternate domain;

transform the first and second amounts of scatterometry data from coordinates in the measurement domain to coordinates of the first overlay target in the alternate domain;

fit a linear model of the principal components of the metrology target to the principal components of the first overlay target; and determine residuals of the fit of the linear model of the principal components of the metrology target to the principal components of the first overlay target, wherein the determining of the first differential measurement signal for the first overlay target is based on a difference between the residuals associated with the first amount of scatterometry data and the residuals associated with the second amount of scatterometry data.

16. The overlay metrology system of claim 15, wherein the metrology target includes a grating structure located in the first layer, the grating structure of the metrology target and the first grating structure of the first overlay target having a process induced asymmetry.

17. The overlay metrology system of claim 15, wherein the metrology target includes a grating structure located in the subsequent layer, the grating structure of the metrology target and the second grating structure of the first overlay target having a process induced asymmetry.

18. The overlay metrology system of claim 10, wherein the first, second, third, and fourth amounts of scatterometry data include scatterometry measurements acquired by a plurality of different metrology techniques.

* * * * *